United States Patent [19]

Yamamoto et al.

[11] Patent Number: 4,705,786
[45] Date of Patent: Nov. 10, 1987

[54] NOVEL OXADIAZOLYL-1,4-DIHYDROPYRIDINES USEFUL AS ANTIHYPERTENSIVE AGENTS

[75] Inventors: Michihiro Yamamoto, Nishinomiya; Yukinori Ozato, Takarazuka; Nobuhiko Tamura; Akira Miyagishi, both of Toyonaka; Youichi Hara, Ibaraki, all of Japan

[73] Assignee: Sumitomo Pharmaceuticals Company, Limited, Osaka, Japan

[21] Appl. No.: 780,974

[22] Filed: Sep. 27, 1985

[30] Foreign Application Priority Data

Oct. 11, 1984 [JP] Japan .................................. 59-213786

[51] Int. Cl.$^4$ .................... A61K 31/41; C07D 401/04; C07D 401/06; C07D 413/04
[52] U.S. Cl. ................................... 514/252; 514/318; 514/341; 546/193; 546/194; 546/277; 546/256; 546/270; 546/271; 546/273; 546/276; 546/278; 546/279; 544/360; 544/295; 544/333; 540/481; 548/131; 548/128
[58] Field of Search ............... 546/193, 194, 277, 256, 546/270; 544/360, 295, 333; 514/341, 252, 318; 540/481

[56] References Cited

U.S. PATENT DOCUMENTS 4,414,213  11/1983  Poindexter et al. ................ 546/275
4,532,248   7/1985  Franckowiak et al. ............. 546/116

FOREIGN PATENT DOCUMENTS 0091726  10/1983  European Pat. Off. ............ 514/252
 116708  12/1983  European Pat. Off. ............ 546/275

OTHER PUBLICATIONS

Opie, L. H., Calcium Antagonists and Cardiovascular Disease, vol. 9, (1984), pp. 165–173.
Bossert et al., 4-Aryldihydropyridines, Angew. Chem. Int. Ed. Engl. 20, 762–769 (1981).
Schramm et al., Novel Dihydropyridines, Nature, vol. 303 (1983), Jun., 535–537.
Goodman et al., The Pharmacological Basis of Therapeutics, p. 28.

Primary Examiner—Henry R. Jiles
Assistant Examiner—J. Richter
Attorney, Agent, or Firm—Stevens, Davis, Miller & Mosher

[57] ABSTRACT

A compound of the formula

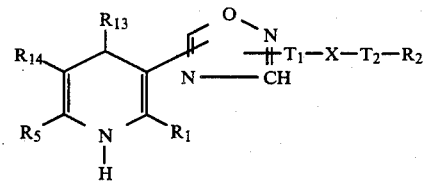

wherein
$T_1$ is lower alkylene, lower alkenylene or a single bond;
X is

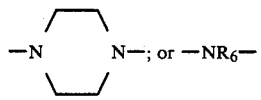

$T_2$ is carbonyl, lower alkylene or a single bond;
$R_2$ is phenyl, phenoxy, pyridyl, pyrimidinyl, furyl, thienyl, lower cycloalkyl or adamantyl;
$R_2$ and $R_6$, when taken together with the nitrogen to which they are attached form pyrrolidinyl, piperidinyl or azacyclooctanyl;
$R_{14}$ is $COOR_8$ or $-R_3R_9$ wherein $T_3$ is lower alkylene and $R_9$ is lower alkoxy, lower cycloalkyl, cyano, polyfluoro-lower alkyl or pyridyl; and
$R_1$ and $R_5$ are each lower alkyl or lower alkenyl, useful in the treatment of cardiovascular diseases.

33 Claims, No Drawings

NOVEL OXADIAZOLYL-1,4-DIHYDROPYRIDINES USEFUL AS ANTIHYPERTENSIVE AGENTS

BACKGROUND OF THE INVENTION

The present invention provides novel heterocyclic compounds which have the calcium antagonistic and vasodilating properties, rendering these compounds useful in the treatment of cardiovascular disorders.

In the past fifteen years a series of 4-aryl-1,4-dihydropyridines has been synthesized and several of them have been investigated as calcium antagonists which are useful in treating myocardial ischemia, infarction or hypertention. Among them the following nifedipine ($R=CH_3$, $2-NO_2$) and nicardipine

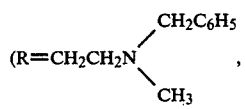

$3-NO_2$) of the formula,

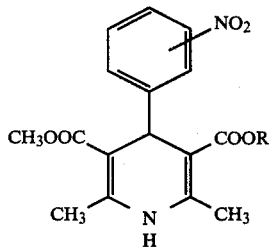

are currently available for clinical uses.

There has been reported a few prior art related to the 1,4-dihydropyridines having a heterocyclic group at the 3- or 5-position of the pyridine ring. Poindexter, et al., U.S. Pat. No. 4,414,213 patented Nov. 8, 1983 disclose the dihydropyridines substituted at 5-position by 4,5-dihydro-2-oxazolyl. Schönafinger, et al., Eur. Pat. Appl. No. 116,708 laid open Aug. 29, 1984 disclose the dihydropyridines which relate to the instant invention, wherein the heterocyclic ring at 5-position is oxadiazolyl, thiadiazolyl or thiazolyl optionally bearing $C_1$–$C_4$ alkyl, $C_1$–$C_4$ alkylthio, $C_7$–$C_8$ aralkyl, $C_2$–$C_5$ alkoxyalkyl, $C_3$ or $C_6$ cycloalkyl, aminocarbonylmethylthio, methoxycarbonyl, ethoxycarbonyl or phenyl. The European Patent noted above also describes that the most preferable heterocyclic substituents include 1,3,4-oxadiazol-2-yl, 5-methyl-1,3,4-oxadiazol-2-yl, 5-ethyl-1,3,4-oxadiazol-2-yl, 3-methyl-1,2,4-oxadiazol-5-yl, 3-ethyl-1,2,4-oxadiazol-5-yl and 3-benzyl-1,2,4-oxadiazol-5-yl. Meyer reported in Calcium Antagonists and Cardiovascular Diseases, edited by Opie, L. H., Chapter 15 (1984) structure-activity relationships in the calcium antagonistic 1,4-dihydropyridines, where it is particularly concluded that carboxylic acid ester functions are optimal substituents at 3- and 5-position of the pyridine ring.

SUMMARY AND DETAILED DESCRIPTION OF THE INVENTION

The present invention pertains to novel oxadiazolyl-1,4-dihydropyridines and analogues thereof, and processes for preparation thereof.

More particularly, the present invntion provides the compounds of the formula,

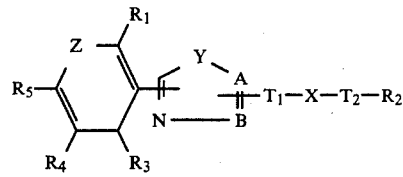

and a pharmaceutically acceptable acid addition salt thereof wherein either A or B is nitrogen and the other is carbon; $T_1$ is lower alkylene or lower alkenylene each of which may contain a phenylene, or a single bond; $T_2$ is carbonyl, lower alkylene which may bear an aryl, or a single bond; X is a radical

(wherein $R_6$ is hydrogen, lower alkyl, lower cycloalkyl-lower alkyl, aralkyl),

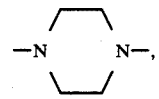

—S—, —S(O)— or —$SO_2$—; Y is oxygen or sulfur; Z is a radical

(wherein $R_7$ is hydrogen or lower alkyl) or, in case either $R_1$ or $R_5$ is amino, Z is oxygen; either $R_1$ or $R_5$ is lower alkyl, lower alkenyl or halo-lower alkyl and the other is lower alkyl, lower alkenyl, halo-lower alkyl, hydroxy-lower alkyl, lower alkoxy-lower alkyl, lower alkanoyloxy-lower alkyl, di-lower alkoxy-lower alkyl, formyl, cyano or amino; $R_2$ is aryl, aryloxy, 5 or 6-membered unsaturated heterocyclic group, lower cycloalkyl or adamantyl, and in case X is a radical,

the group

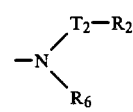

may be a 5- to 8-membered saturated N-containing heterocyclic group, which may contain an o-phenylene and may further bear a lower alkyl, oxo, aryl, aralkyl or aroyl; $R_3$ is aryl, pyridyl which may form N-oxide, thienyl, furyl, 2,1,3-benzoxadiazolyl, lower alkyl, lower cycloalkyl, aralkyl or benzhydryl, wherein these aryl and heterocyclic group may be optionally substituted by one or two same or different substituents which is selected from the group consisting of halogen, nitro, trifluoromethyl, cyano, lower alkyl, lower alkoxy, polyfluoro-lower alkoxy and benzyloxy; and $R_4$ is hydrogen, cyano, carbamoyl, lower alkanoyl, a group —$COOR_8$ [wherein $R_8$ is a saturated or unsaturated $C_1$-$C_{10}$ hydrocarbon radical, a group —$T_3$—$R_9$ (wherein $T_3$ is lower alkylene and $R_9$ is lower alkoxy, lower cycloalkyl, cyano, polyfluoro-lower alkyl aryl or pyridyl) or a group

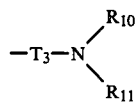

wherein $T_3$ is lower alkylene and $R_{10}$ and $R_{11}$ are lower alkyl)] or a group

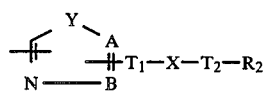

(wherein A, B, $R_2$, $T_1$, $T_2$, X and Y are as defined above).

In the compounds of the above formula (I) and elsewhere in the specification, the terms "alkyl", "alkenyl", "alkylene" and "alkenylene" mean both straight- and branched $C_1$-$C_6$ hydrocarbon chains, and the lower alkyl may be $C_1$-$C_6$ alkyl such as methyl, ethyl, n-propyl, isopropyl, n-butyl, isobutyl, tert-butyl, n-pentyl, isopentyl, neopentyl, n-hexyl and the like. The lower alkenyl may be $C_2$-$C_6$ alkenyl such as vinyl, allyl, propenyl, isopropenyl, 2-methylpropenyl, 2-butenyl, 3-butenyl, 3-methyl-2-butenyl and the like. The examples of the lower alkylene and alkenylene may be illustrated as follows:

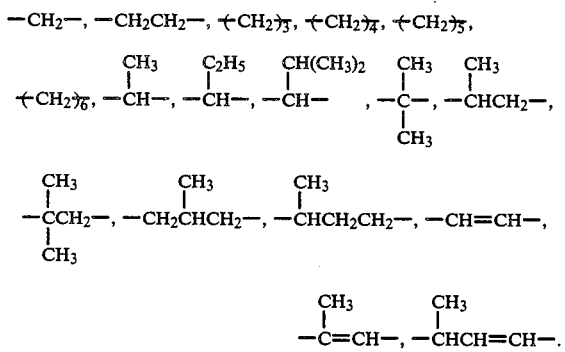

The lower cycloalkyl may be $C_3$-$C_6$ alicyclic group such as cyclopropyl, cyclobutyl, cyclopentyl and cyclohexyl. The lower alkoxy may be $C_1$-$C_6$ alkoxy such as methoxy, ethoxy, n-propoxy, isopropoxy, n-butoxy, isobutoxy, tert-butoxy and n-amyloxy. The lower alkanoyl may be $C_2$-$C_5$ alkanoyl such as acetyl, propionyl, butyryl, pivaloyl and the like and the lower alkanoyloxy may be $C_2$-$C_5$ alkanoyloxy such as acetoxy, propionyloxy, butyryloxy, pivaloyloxy and the like. The terms such as lower cycloalkyl-lower alkyl, halo-lower alkyl, hydroxy-lower alkyl, lower alkoxy-lower alkyl, lower alkanoyloxy-lower alkyl and di-lower alkoxy-lower alkyl mean the $C_1$-$C_6$ alkyl moiety which is substituted at the optional position by the lower cycloalkyl, halogen, hydroxy, lower alkoxy or lower alkanoyloxy, respectively. The term "halogen" includes all four halogens, i.e., fluorine, chlorine, bromine and iodine. The term "aryl" means the substituted or unsubstituted aromatic hydrocarbon radical such as phenyl, 2-fluorophenyl, 3-fluorophenyl, 4fluorophenyl, 2-chlorophenyl, 3-chlorophenyl, 4-chlorophenyl, 3-bromophenyl, 2,3-dichlorophenyl, 3,4-dichlorophenyl, 2,4-difluorophenyl, 2-methylphenyl, 3-methylphenyl, 4-methylphenyl, 2-methoxyphenyl, 3-methoxyphenyl, 4-methoxyphenyl, 3,4-dimethoxyphenyl, 3,4-methylenedioxyphenyl, 2,3,4-trimethoxyphenyl, 2-cyanophenyl, 3-cyanophenyl, 2-nitrophenyl, 3-nitrophenyl, 3-methylsulfonylphenyl, 4methylsulfonylphenyl, 2-trifluoromethylphenyl, 3-trifluoromethylphenyl, 4-hydroxyphenyl, 1-naphthyl, 2-naphthyl and the like. The term "aralkyl" means the lower alkyl which is substituted by an aryl as defined above. The aryloxy means phenoxy or a substituted phenoxy wherein the substituted phenyl moiety is as defined above. The aroyl may be benzoyl or a substituted benzoyl such as 4-fluorobenzoyl, 4-chlorobenzoyl, 4-methylbenzoyl, 4-methoxybenzoyl, 3,4-methylenedioxybenzoyl and the like. The polyfluoro-lower alkyl may, for example, be difluoromethyl, trifluoromethyl, 2,2,2-trifluoroethyl, 2,2,3,3-tetrafluoropropyl or 2,2,3,3,3-pentalfuoropropyl. The polyfluoro-lower alkoxy may, for example, be difluoromethoxy, trifluoromethoxy, 2,2,2-trifluoroethoxy, 2,2,3,3-tatrafluoropropoxy or 2,2,3,3,3-pentafluoropropoxy. The 5- or 6-membered unsaturated heterocyclic group defined in $R_2$ may, for example, be pyrrolyl, pyrazolyl, imidazolyl, thienyl, furyl, thiazolyl, oxazolyl, isoxazolyl, pyridyl, pyrimidyl or the like, e.g., 1-pyrrolyl, 2-pyrrolyl, 1-pyrazolyl, 3-pyrazolyl, 1-imidazolyl, 2-imidazolyl, 2-thienyl, 2-furyl, 2-thiazolyl, 2-oxazolyl, 5-isoxazolyl, 2-pyridyl, 3-pyridyl, 4-pyridyl or 2-pyrimidyl. The 5- to 8-membered saturated N-containing heterocyclic group formed by the group

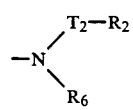

may, for example, be pyrrolidinyl, 2-oxopyrrolidinyl, piperidinyl, 4-phenylpiperidinyl, 4-benzylpiperidinyl, 4-(p-fluorobenzoyl)piperidinyl, homopiperidinyl, azacyclooctanyl, 3-azabicyclo[3,2,2]nonanyl, indolinyl, isoindolinyl, 1,2,3,4-tetrahydroquinolyl, 1,2,3,4-tetrahydroisoquinolyl, 7,8-dichloro-1,2,3,4-tetrahydroisoquinolyl or the like.

Preferred compounds encompassed by the present invention include those of the aforesaid formula (I) wherein X is a radical

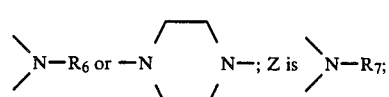

Z is

and R₄ is a group —COOR₈.

More preferred class of compounds falling within the scope of the present invention are those of the formula (I) wherein X is a radical

(wherein R₆ is hydrogen, lower alkyl or aralkyl) or

Z is

(wherein R₇ is hydrogen); T₁ is lower alkylene; T₂ is lower alkylene or a single bond; R₁ and R₅ are lower alkyl; R₂ is aryl, pyridyl, thienyl or furyl; R₃ is aryl; R₄ is a group —COOR₈ (wherein R₈ is a saturated C₁-C₁₀ hydrocarbon radical or T₃-R₉ (wherein T₃ is lower alkylene and R₉ is lower alkoxy, lower cycloalkyl or pyridyl)).

The present invention also includes acid addition salts of the compounds of the formula (I) formed with pharmaceutically acceptable acids. Such acids include both organic and inorganic acids, e.g., hydrochloric, hydrobromic, hydroiodic, sulfuric, phosphoric, methanesulfonic, acetic, pivalic, oxalic, maleic, fumaric, malic, succinic, tartaric, citric, ascorbic, glutamic, aspartic, stearic, palmitic acids and the like.

The compounds of the aforesaid formula (I) can exist as stereoisomers due to an asymmetric carbon at 4-position of the dihydropyridine ring. Accordingly, the optically active enantiomers may be obtained according to known methods such as the resolution of the racemate and high pressure liquid chromatography. The optically active compounds of the formula (I) are also within the scope of the present invention.

The oxadiazolyl-1,4-dihydropyridines and their analogues of the formula (I) have not been reported in any literature. They have been found to possess prominent calcium antagonistic property, namely, inhibiting action of Ca²⁺ influx into vascular smooth muscle cells through voltage-dependent calcium channels. In particular, they exhibit potent antihypertensive activity with long duration of action due to peripheral vasodilation.

Our earlier U.S. Pat. Appl. No. 469,511 or Eur. Pat. Apple. No. 91,726 describes that the 1,2,4-oxadiazoles of the formula.

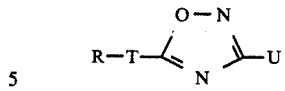

wherein U is an optionally present one of a specific range of aliphatic and aromatic groups; R is one of a specific range of aromatic groups; and T is optionally substituted lower alkylene or lower alkenylene, possess potent antiinflammatory activity comparable to the known acidic antiinflammatory compounds of the formula,

R—T—COOH wherein R and T are as defined above, which are deemed the parent compounds of the 1,2,4-oxadiazoles described above. On the basis of this findings, we anticipated that the 1,2,4-oxadiazolyl group might be a new bioisostere of the carboxylic acid group, therefore, we attempted the bioisosteric replacements for the known 1,4-dihydropyridine 3,5-dicarboxylic acid esters to develop novel and useful drugs. The concept of bioisosterism has been described in the literature (see, e.g., C. W. Thornber, Chemical Society Reviews, Vol. 8, 563 (1979)). In order to confirm this hypothesis, the oxadiazolyl-1,4-dihydropyridines were assayed for several cardiovascular in vitro and in vivo tests, and they were surprisingly found not only to show potent calcium antagonistic activity and antihypertensive vasodilating activity but also to have inhibitory effects on norepinephrine-induced contractions of the isolated rabbit aortic strip potentiated by ouabain.

The in vitro calcium antagonistic activity of the subject compounds of the formula (I) was evaluated according to substantially the same method as that of Toda et al., J. Pharmacol. Exp. Ther. 181, 512 (1972) and ibid., 191, 139 (1974).

Male Wistar rats weighing 300–400 g were stunned by a sharp blow to the head. The isolated strips of the descending aorta were-fixed vartically in a 50 ml organ both containing Krebs-Henseleit solution maintained at 37° C. and saturated with a 95% O₂+5% CO₂ gas mixture. Isometric tension was measured with a foree-displacement transducer and recorded on a polygraph recorder. During a 60-90 min equilibration period the resting tension was repeatedly adjusted to 1 g. The vessels having ability to potassium-induced contractions were exposed to a Ca²⁺-free medium for 30 min and then to 25 mM K⁺ solution. When a contractile plateau was reached, Ca²⁺ was added, and the cumulative response to 0.25, 0.5 and 4 mM Ca²⁺ was recorded. After wash-out and a equilibration period with renewed testing of contractile ability, the preparations were once more exposed to Ca²⁺-free medium. The test compound was added to the organ bath 5 min before administration of potassium. Calcium was cumulatively added once again and the contractile response so obtained was expressed in percent of the contraction elicited by 4 mM Ca²⁺. Dose-response curves for Ca²⁺ were carried out cumulatively in the absence or presence of increasing concentrations of test compound. The pA₂ values were calculated by the method of Arunlakshana et al., Brit. J. Pharmacol., 14, 48 (1959). Results in this test with the reference compounds are given in Table I.

TABLE I

| Compound | pA$_2$ |
| --- | --- |
| A. Methyl 1,4-dihydro-2,6-dimethyl-3-(3-piperidinomethyl-1,2,4-oxadiazol-5-yl)-4-(3-nitrophenyl)pyridine-5-carboxylate hydrochloride | 10.51 |
| B. Methyl 1,4-dihydro-2,6-dimethyl-3-(3-piperidinomethyl-1,2,4-oxadiazol-5-yl)-4-phenylpyridine-5-carboxylate hydrochloride | 9.44 |
| C. Methyl 1,4-dihydro-2,6-dimethyl-3-(3-piperidinomethyl-1,2,4-oxadiazol-5-yl)-4-(3,4-dichlorophenyl)pyridine-5-carboxylate hydrochloride | 9.89 |
| D. Methyl 1,4-dihydro-2,6-dimethyl-3-[3-(N—benzyl-N—methylamino)methyl-1,2,4-oxadiazol-5-yl]-4-(3-nitrophenyl)-pyridine-5-carboxylate hydrochloride | 9.73 |
| E. Methyl 1,4-dihydro-2,6-dimethyl-3-[3-(α-methylbenzylamino)methyl-1,2,4-oxadiazol-5-yl]-4-(3-nitrophenyl)-pyridine-5-carboxylate citrate | 10.34 |
| F. Methyl 1,4-dihydro-2,6-dimethyl-3-[3-[N—(3,4-dimethoxyphenethyl)-N—methylamino]methyl-1,2,4-oxadiazol-5-yl]-4-(3-nitrophenyl)pyridine-5-carboxylate hydrochloride | 10.02 |
| G. Isopropyl 1,4-dihydro-2,6-dimethyl-3-[3-(N—benzyl-N—methylamino)methyl-1,2,4-oxadiazol-5-yl]-4-(3-nitrophenyl)-pyridine-5-carboxylate hydrochloride | 9.45 |
| R1. Methyl 1,4-dihydro-2,6-dimethyl-3-(3-methyl-1,2,4-oxadiazol-5-yl)-4-(3-nitrophenyl)pyridine-5-carboxylate | 7.49 |
| R2. Dimethyl 1,4-dihydro-2,6-dimethyl-4-(2-nitrophenyl)-3,5-dicarboxylate: nifedipine | 9.11 |
| R3. 2-(N—Benzyl-N—methylamino)ethyl methyl 1,4-dihydro-2,6-dimethyl-4-(3-nitrophenyl)pyridine-3,5-dicarboxylate: nicardipine | 9.38 |

The representative compounds A–G of the present invention were found to have more potent calcium antagonistic activity than the reference compounds R1-3. The compound R1 which is disclosed in the aforesaid Eur. Pat. Appl. 116,708, was 100–1000 times less potent than the subject compounds.

The compounds having potent calcium antagonistic activity were then examined by the in vivo method for demonstrating antihypertensive vasodilating activity. The anesthetized and ganglion-blocked rats whose blood pressure were maintained by an intravenous infusion of angiotensin II were prepared and the test compounds were evaluated according to substantially the same method as that of Deitchman et al., J. Pharmacol Methods, 3, 311 (1980). In this experimental model calcium antagonists were revealed to cause significant and dose-dependent reductions in mean arterial blood pressure. For example, intravenous administrations of 0.01 mg/kg and 0.003 mg/kg compound D in Table I were found to show dose-dependently more potent and long acting antihypertensive effects in comparison with nifedipine and nicardipine.

Antihypertensive activity of the compound D was further confirmed by the tests of single oral administration to both normotensive rats and spontaneous hypertensive rats (SHR). In the SHR the compound D 1 mg/kg exhibited about the same antihypertensive activity as that of nicardipine 3 mg/kg and the effect of the compound D continued much longer than that of nicardipine.

The hypotensive potency of the compound D was also compared with that of nicardipine by administering to the SHR for 4 weeks at 15 mg/kg/day, po. In this experiment the compound D showed apparent antihypertensive activity with slight decrease of heart rate, whereas nicardipine did no significant effects.

In the physiological saline loaded rats, the compound D 3 mg/kg, po was seen to have about the same diuretic activity as that of nicardipine 10 mg/kg, po.

Thus the results obtained above indicate that the compound D may exhibit excellent antihypertensive effects with low dose and long interval of administration in comparison with the known 1,4-dihydropyridine dicarboxylate.

In addition the compounds of the present invention were found to possess inhibitory effects on norepinephrine-induced contractions of the isolated rabbit aortic strip potentiated by ouabain.

Sodium permeability in vascular smooth muscles is supposed to be an important determinant of vascular tone, since an increase of intracellular Na$^+$ concentration induces the development of tension in isolated vascular strips (see Van Breeman et al., Pharmacol, Rev., 30, 167 (1979)). Recently De Wardener et al., The Lancet I, 1450 (1982) has described the hypothesis that the rise in peripheral resistance in inherited hypertension is due largely to the observed rise in the circulating level of a sodium-transport inhibitor such as endogenous ouabain-like substance. It is well known that cardiac glycosides sensitize vascular tissue to agonists via a direct effect on the smooth muscle, and that it has been found that low doses of the specific sodium-pump inhibitor, i.e. ouabain sensitize normal rabbit aorta to norepinephrine.

Thus the compounds of the present invention such as D and F in Table I were found to inhibit these contractions at a concentration of 0.01 μM, whereas nifedipine and nicardipine failed to inhibit at concentrations as high as 0.1 μM.

These results suggest that the oxadiazolyl-1,4-dihydropyridine derivatives of the present invention may decrease the intracellular accumulation of sodium in vascular smooth muscle, and therefore, provide beneficial effects for intrinsic improvement of essential hypertension.

In order to treat or prevent cardiovascular diseases such as hypertension, arteriosclerosis, myocardial ischemia and infarction, heart failure, and peripheral circulatory disorders in mammals including human beings, the compounds of the present invention may be employed in the form of pharmaceutical composition adapted for enteral or parenteral administration. Accordingly, said compounds can be combined with solid or liquid pharmaceutical carriers, and then formulated in the form of tablets, capsules, soft gelatin capsules, powder packets, granules, suspensions, syrups, suppositories and the like for enteral use, and ointment, cream, jelly, poultices, liquids, emulsions, injections and the like for parenteral use. This pharmacentical preparation may also contain non-toxic auxiliary substances such as preservatives, stabilizers, wetting agents, detergents, buffers and the like. The pharmaceutical composition containing an effective amount of at least one of the compounds of the formula (I) as an active ingredient can be prepared according to the known formulation methods.

In the treatment of the cardiovascular diseases in man, the compound of the present invention may be generally administered in an amount of from 0.05 mg/kg/day to 20 mg/kg/day, preferably from 0.1 mg/kg/day to 4 mg/kg/day depending upon the sympton and the age of the patient, the route of administration, and the particular compound employed.

The oxadiazolyl-1,4-dihydropyridine derivatives and their analogues of the aforesaid formula (I) can be prepared according to known processes such as Hantzsch ester synthesis and the modification methods thereof, e.g. see Prous et al., Drugs of the Future, Vol. VI, No. 7, 427 (1981).

Said processes of the present invention comprise:

(a) reacting a compound of the formula, $$R_1-CO-CH_2-\underset{N\underline{\quad\quad}B}{\overset{Y\diagdown A}{\underset{\parallel}{\fbox{\phantom{X}}}}}-T_1-X-T_2-R_2 \quad (II)$$

wherein A, B, $T_1$, $T_2$, X, Y, $R_1$ and $R_2$ are as defined above, with both an aldehyde of the formula, $$R_3-CHO \quad (III)$$

wherein $R_3$ is as defind above, and an enamine of the formula, $$R_4-CH=\underset{NH-R_7}{\overset{|}{C}}-R_5 \quad (IV)$$

wherein $R_4$, $R_5$ and $R_7$ are as defined above, to yield a compound of the formula, $$\text{(Ia)}$$

wherein A, B, $T_1$, $T_2$, X, Y, $R_1$, $R_2$, $R_3$, $R_4$, $R_5$ and $R_7$ are as defined above, (b) reacting a compound of the formula, $$\underset{R_7-NH}{\overset{R_1-C=CH-}{}}\underset{N\underline{\quad\quad}B}{\overset{Y\diagdown A}{\underset{\parallel}{\fbox{\phantom{X}}}}}T_1-X-T_2-R_2 \quad (V)$$

wherein A, B, $T_1$, $T_2$, X, Y, $R_1$, $R_2$ and $R_7$ are as defined above, with a compound of the formula, $$R_3-CH=\underset{R_4}{\overset{|}{C}}-CO-R_5 \quad (VI)$$

wherein $R_3$, $R_4$ and $R_5$ are as defined above, to yield a compound of the aforesaid formula (Ia), (c) Reacting a compound of the formula, $$R_1-CO-CH_2-\underset{N\underline{\quad\quad}B}{\overset{Y\diagdown A}{\underset{\parallel}{\fbox{\phantom{X}}}}}-T_1-X-T_2-R_2 \quad (II)$$

wherein A, B, $T_1$, $T_2$, X, Y, $R_1$ and $R_2$ are as defined above, both with a compound of the formula, $$R_3-CH=\underset{R_4}{\overset{|}{C}}-CO-R_5 \quad (VI)$$

wherein $R_3$, $R_4$ and $R_5$ are as defined above, and ammonia or an amine of the formula, $$R_7-NH_2 \quad (VII)$$

wherein $R_7$ is as defined above, to yield a compound of the aforesaid formula (Ia), (d) in case $R_4$ of the aforesaid formula (I) is the group $$-\underset{N\underline{\quad\quad}B}{\overset{Y\diagdown A}{\underset{\parallel}{\fbox{\phantom{X}}}}}-T_1-X-T_2-R_2$$

(wherein A, B, X, Y, $T_1$, $T_2$ and $R_2$ are as defined above); and $R_1$ and $R_5$ are the same substituent, reacting two molar equivalents of a compound of the formula, $$R_1-CO-CH_2-\underset{N\underline{\quad\quad}B}{\overset{Y\diagdown A}{\underset{\parallel}{\fbox{\phantom{X}}}}}-T_1-X-T_2-R_2 \quad (II)$$

wherein A, B, $T_1$, $T_2$, X, Y, $R_1$ and $R_2$ are as defined above, both with an aldehyde of the formula, $$R_3-CHO \quad (III)$$

wherein $R_3$ is as defined above, and ammonia or an amine of the formula, $$R_7-NH_2 \quad (VII)$$

wherein $R_7$ is as defined above, to yield a compound of the formula, $$\text{(Ib)}$$

wherein A, B, $T_1$, $T_2$, X, Y, $R_1$, $R_2$, $R_3$ and $R_7$ are as defined above, (e) Reacting a compound of the formula, $$\text{(Ic)}$$

wherein A, B, $T_1$, $T_2$, X, Y, $R_1$, $R_2$, $R_3$, $R_4$ and $R_5$ are as defined above, with a reactive ester of an alcohol of the formula, $$R_{12}-OH \quad (VIII)$$

wherein R₁₂ is lower alkyl, to yield a compound of the formula,

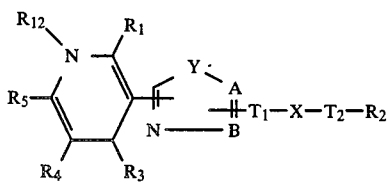
(Id)

wherein A, B, T₁, T₂, X, Y, R₁, R₂, R₃, R₄, R₅ and R₁₂ are as defined above, (f) in case Z of the aforesaid formula (I) is oxygen and either R₁ or R₅ is amino, reacting a compound of the formula,

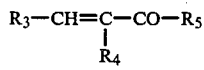
(VI)

wherein R₃, R₄ and R₅ are as defined above, with a nitrile of the formula,

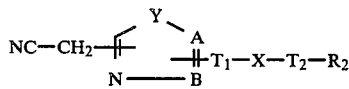
(IX)

wherein A, B, T₁, T₂, X, Y and R₂ are as defined above, or reacting a compound of the formula,

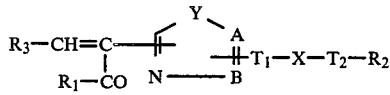
(X)

wherein A, B, T₁, T₂, X, Y, R₁, R₂ and R₃ are as defined above, with a nitrile of the formula,

R₄—CH₂—CN (XI)

wherein R₄ is as defined above, to yield a oxadiazolyl-4H-pyran derivative of the formula,

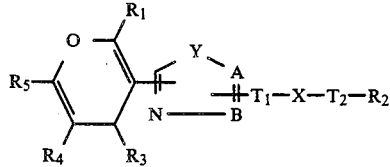
(Ie)

wherein A, B, T₁, T₂, X, Y, R₁, R₂, R₃, R₄ and R₅ are as defined above, (g) in case Z of the aforesaid formula (I) is a radical

and either R₁ or R₅ is amino, reacting a compound of the formula,

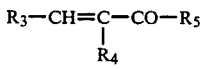
(VI)

wherein R₃, R₄ and R₅ are as defined above, with a compound of the formula,

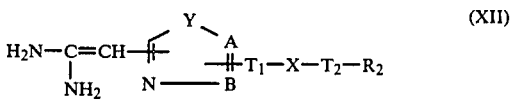
(XII)

wherein A, B, T₁, T₂, X, Y and R₂ are as defined above, or reacting a compound of the formula,

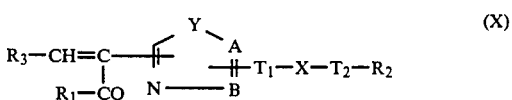
(X)

wherein A, B, T₁, T₂, X, Y, R₁, R₂ and R₃ are as defined above, with a compound of the formula,

(XIII)

wherein R₄ is as defined above, to yield a compound of the formula,

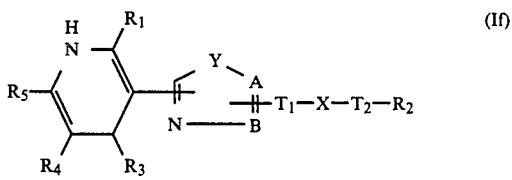
(If)

wherein A, B, T₁, T₂, X, Y, R₁, R₂, R₃, R₄ and R₅ are as defined above, (h) reacting an alcohol of the formula,

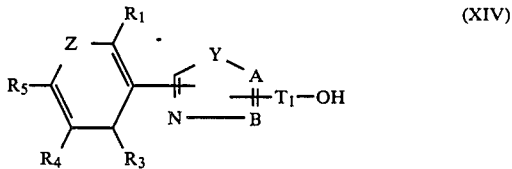
(XIV)

wherein A, B, T₁, Y, Z, R₁, R₃, R₄ and R₅ are as defined above, or its reactive ester with a compound of the formula,

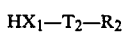
HX₁—T₂—R₂ (XV)

wherein X₁ is a radical

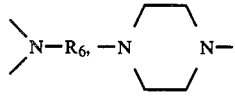

or —S—; and T₂, R₂ and R₆ are as defined above, or its alkali salt to yield a compound of the formula,

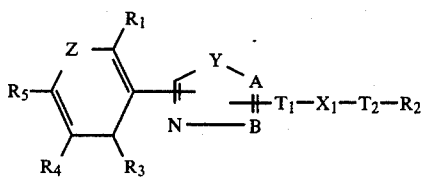

(Ig)

wherein A, B, $T_1$, $T_2$, $X_1$, Y, Z, $R_1$, $R_2$, $R_3$, $R_4$ and $R_5$ are as defined above or (i) in case $R_4$ of the aforesaid formula (I) is a group —$COOR_8$, reacting a carboxylic acid of the formula,

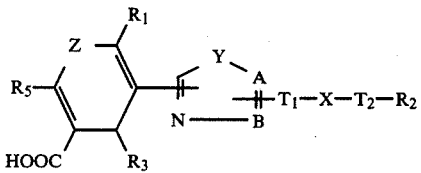

(Ih)

wherein A, B, $T_1$, $T_2$, X, Y, Z, $R_1$, $R_2$, $R_3$ and $R_5$ are as defined above, or its reactive derivative with an alcohol of the formula, $$R_8-OH \qquad (XVI)$$

wherein $R_8$ is as defined above, to yield a compound of the formula,

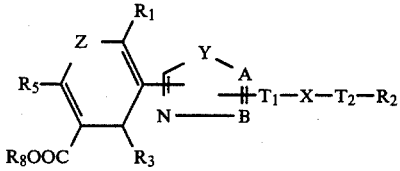

(Ii)

wherein A, B, $T_1$, $T_2$, X, Y, Z, $R_1$, $R_2$, $R_3$, $R_5$ and $R_8$ are as defined above.

The above-mentioned methods (a)–(i) for preparing the compounds of the present invention will be explained in detail below.

In the method (a), an equivalent of a compound of the aforesaid formula (II) is reacted with both an aldehyde of the formula (III) and an enamine of the formula (IV) in an inert solvent. Suitable solvents include alcohols, e.g., methanol, ethanol, n-propanol, isopropanol, tert-butanol, n-hexanol, cyclohexanol; ethers, e.g., tetrahydrofuran (THF), diethyl ether, dioxane, 1,2-dimethoxyethane, ethylene glycol monomethyl ether, diethylene glycol dimethyl ether; acetonitrile, dimethylformamide (DMF), dimethylsulfoxide, pyridine, water and a mixture thereof. This reaction is effected at a temperature within the range of from room temperature to 150° C., preferably at reflux temperature, and if necessary, under increased pressure.

A compound of the formula (II), which is novel and important starting material of the present invention can be prepared according to substantially the same procedure reported in the known literature (see, e.g., B. Kübel, Monatshefte für chemie, 113, 781-803 (1982). Certain enamines of the formula (IV) are well known and are described in the literature (see, e.g., A. C. Cope, J. Amer, Chem. Soc. 67, 1017 (1945)).

In the method (b), an equivalent of a compound of the aforesaid formula (V) is heated to react with a compound of the formula (VI) in an inert solvent. The reaction may be preferably effected at the boiling point of the suitable solvent as described in the method (a). The intermediate compound of the formula (V) can be prepared by reacting a compound of the aforesaid formula (II) with ammonia or an amine of the formula (VII) in the presence of a Lewis acid such as zinc chloride, titanium tetrachloride, boron trifluoride etherate, phosphorus oxychloride and the like. The compound of the formula (V) wherein $R_7$ is hydrogen, may be also prepared by reacting a compound of the formula,

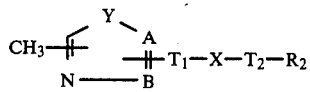

(XVII)

wherein A, B, $T_1$, $T_2$, X, Y and $R_2$ are as defined above, first with lithium diisopropylamide and then with a nitrile of the formula, $$R_1-CN \qquad (XVIII)$$

wherein $R_1$ is as defined above, followed by quenching with ammonium chloride solution. The another intermediate of the formula (VI) is known as a Knoevenagel condensation product, which is obtained by reacting an aldehyde of the aforesaid formula (III) with a ketone of the formula, $$R_4-CH_2-CO-R_5 \qquad (XIX)$$

wherein $R_4$ and $R_5$ are as defined above.

In the method (c), an equivalent of a compound of the aforesaid formula (II) is reacted with both a compound of the formula (VI) and ammonia or an amine of the formula (VII) in an inert solvent. The reaction can be effected under almost the same conditions as employed in the method (a).

In the method (d), 2 molar equivalents of a compound of the formula (II) is reacted both with an aldehyde of the formula (III) and ammonia or an amine of the formula (VII) in an inert solvent. This reaction can be also conducted under the same conditions as employed in the method (a).

In the method (e), a compound of the formula (Ic) is reacted with a reactive ester of an alcohol of the aforesaid formula (VIII) in an inert solvent in the presence of a basic condensing agent. Alternatively, the compound of the formula (Ic) is treated in an inert solvent with a basic condensing agent to form a metal salt, which is then reacted with the reactive ester of the alcohol. Suitable basic condensing agents include, for example, sodium hydride, sodium amide, butyllithium, sodium methoxide, sodium ethoxide and the like. Suitable solvents include, for example, toluene, xylene, THF, dioxane, 1,2-dimethoxyethane, DMF, dimethylacetamide, dimethylsulfoxide. The reaction is effected at a temperature in the range between room temperature and the boiling point of the solvent employed.

In the method (f), a compound of the aforesaid formula (VI) is reacted with a nitrile of the formula (IX), alternatively, a compound of the formula (X) is reacted with a nitrile of the formula (XI) in an inert solvent as described in the method (a). The reaction may be preferably effected by heating in the presence of a base catalyst such as piperidine.

In the method (g), a compound of the aforesaid formula (VI) is reacted with an amidine compound of the formula (XII), alternatively, a compound of the formula (X) is reacted with an amidine compound of the formula (XIII) in an inert solvent as described in the method (a). The reaction may be preferably effected by heating under reflux, in the solvent employed. The intermediate amidine compounds of the formulae (XII) and (XIII) can be prepared by reacting the nitrile compounds of the formulae (IX) and (XI) with an alcohol, respectively, in the presence of an acid catalyst such as hydrogen chloride or sulfuric acid, followed by reacting with ammonia or ammonium chloride. The free amidine suitably employed for the reaction is conveniently prepared by treating the amidine acid addition salt with an appropriate base such as sodium methoxide or sodium ethoxide.

In the method (h), an alcohol compound of the aforesaid formula (XIV) or its reactive ester is reacted in an inert solvent with a compound of the formula (XV) or its alkali salt at room temperature or an elevated temperature in the presence of a basic condensing agent. Suitable reactive esters of the alcohol (XIV) include, for example, chloride, bromide, iodide, p-toluenesulfonate, methanesulfonate, trichloromethanesulfonate and the like. Suitable solvents include, for example, methanol, ethanol, isopropanol, n-butanol, acetone, methyl isobutyl ketone, acetonitrile, THF, dioxane, DMF, dimethylsulfoxide, water, and a mixture thereof. A great excess of the compound of the formula (XV) may be employed as a reaction solvent, if it is liquid form. Suitable basic condensing agent include, for example, sodium hydroxide, potassium hydroxide, potassium carbonate, sodium hydride, sodium methoxide, sodium ethoxide, triethylamine, diisopropylethylamine, N,N-dimethylaniline, N,N-dimethylbenzylamine, pyridine and the like. The starting compound of the formula (XIV) or its reactive ester may be readily prepared by reacting a compound of the formula,

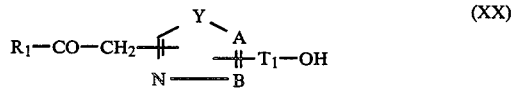

(XX)

wherein A, B, T$_1$, Y and R are as defined above, or its reactive ester with both an aldehyde of the aforesaid formula (III) and an enamine of the formula (IV).

In the method (i), a carboxylic acid of the aforesaid formula (Ih) or its reactive derivative is reacted with an alcohol of the formula (XVI) in an inert solvent at a temperature within the range of from room temperature to reflux temperature. Suitable reactive derivatives of the carboxylic acid (Ih) include, e.g., a carboxylic acid halide such as chloride, bromide or iodide, carboxylic acid anhydride including a mixed anhydride, an activated ester and the like. The reaction of this method may be preferably effected in the presence or absence of a basic condensing agent or an accelerator. Suitable inert solvents include, for example, benzene, toluene, methylene chloride, chloroform, ether, dioxane, dimethyoxyethane, THF, DMF, pyridine and the like. Suitable basic condensing agents include, for example, triethylamine, N,N-dimethylaniline, pyridine, potassium carbonate and the like. Suitable accelerator for the reaction include, for example, sulfuric acid, hydrochloric acid, p-toluenesulfonic acid, boron trifluoride etherate, magnesium, zinc chloride, sodium acetate, potassium acetate and the like. In case a free carboxylic acid of the formula (Ih) is employed, the reaction may be preferably conducted in the presence of a condensing agent such as N,N'-dicyclohexylcarbodiimide (DCC), 1-hydroxybenzotriazole-DCC, N,N'-carbonyldiimidazole or the like.

The starting carboxylic acid of the formula (Ih) is conveniently prepared by hydrolizing a cyanoethyl ester of the formula,

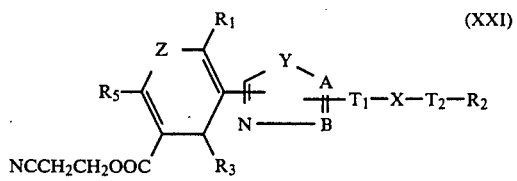

(XXI)

wherein A, B, T$_1$, T$_2$, X, Y, Z, R$_1$, R$_2$, R$_3$ and R$_5$ are as defined above.

The following Examples are given by way of illustration and are not to be construed as limitation of this invention.

EXAMPLE 1

To a solution of 15.0 g of 5-acetonyl-3-chloromethyl-1,2,4-oxadiazole in 50 ml of THF were added dropwise 17.4 g of triethylamine and subsequently 11.0 g of piperidine. The mixture was stirred at room temperature for 24 hours and then heated under reflux for 6 hours. After cooling, the precipitated material was removed by filtration and the filtrate was evaporated in vacuo. The residue was chromatographed on silica gel using chloroform-methanol (20:1, v/v) as eluent to give 10.9 g of 5-acetonyl-3-piperidinomethyl-1,2,4-oxadiazole as a colorless solid, m.p. 66°–67° C.

A mixture of 500 mg of the oxadiazole intermediate prepared above, 240 mg of benzaldehyde and 260 mg of methyl 3-aminocrotonate in 5 ml of isopropyl alcohol was heated under reflux for 8 hours and then concentrated to dryness in vacuo. The residue was chromatographed on silica gel using chloroform-methanol (20:1, v/v) as eluent to give 600 mg of methyl 1,4-dihydro-2,6-dimethyl-3-(3-piperidinomethyl-1,2,4-oxadiazol-5-yl)-4-phenylpyridine-5-carboxylate as pale yellow crystals, mp. 187°–188° C. (decomp.).

EXAMPLES 2 TO 15

According to substantially the same procedure as that of Example 1, there were obtained the following oxadiazolylpyridine derivatives from the corresponding benzaldehydes as listed in Table II.

TABLE II

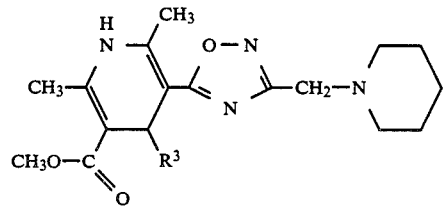

| Example | R$_3$ | Physical Data |
|---|---|---|
| 2 | 3-nitrophenyl | m.p. 155° C. (decomp., HCl salt) |
| 3 | 2-nitrophenyl | m.p. 172° C. |
| 4 | 2-tolyl | m.p. 191° C. (decomp.) |
| 5 | 3-trifluoromethylphenyl | m.p. 123–124° C. |
| 6 | 2-trifluoromethylphenyl | m.p. 202.5–203.5° C. |
| 7 | 2-cyanophenyl | m.p. 169° C. |
| 8 | 2-methoxyphenyl | m.p. 149° C. |

TABLE II-continued

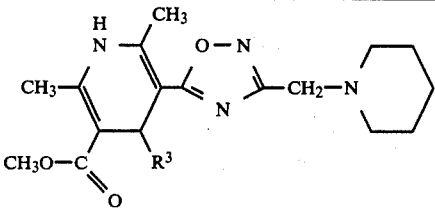

| Example | R₃ | Physical Data |
|---|---|---|
| 9 | 3,4-dichlorophenyl | IR $\nu_{max}^{Nujol}$ cm⁻¹: 3300, 1680, 1640, 1540, 1490 |
| 10 | 3-pyridyl | m.p. 180° C. |
| 11 | 1-naphthyl | IR $\nu_{max}^{Nujol}$ cm⁻¹: 3320, 1690, 1650, 1545, 1490 |
| 12 | 2-nitro-5-thienyl | IR $\nu_{max}^{neat}$ cm⁻¹: 3290, 3200, 1700, 1645, 1530 |
| 13 | 2-nitro-5-furyl | m.p. 145° C. |
| 14 | cyclohexyl | IR $\nu_{max}^{neat}$ cm⁻¹: 3320, 1680, 1640, 1540, 1490 |
| 15 | isopropyl | m.p. 177–179° C. |

EXAMPLE 16

A mixture of 800 mg of 5-acetonyl-3-chloromethyl-1,2,4-oxadiazole, 720 mg of N-methylbenzylamine and 1.0 g of triethylamine in 5 ml of DMF was stirred at room temperature for 8 hours. The reaction mixture was then poured into ice-water and the resultant mixture was extracted with ethyl acetate. The extracts were washed with water, dried over magnesium sulfate and concentrated in vacuo to yield a brown oil. Chromatography on silica gel using chloroform-methanol (20:1, v/v) as eluent afforded 780 mg of 5-acetonyl-3-(N-benzyl-N-methylamino)methyl-1,2,4-oxadiazole as a colorless oil, IR $\nu_{max}^{neat}$ cm⁻¹: 1730, 1635, 1580, 1545, 1450, 1360.

A solution of 520 mg of the oxadiazole intermediate prepared above, 450 mg of 3-nitrobenzaldehyde and 230 mg of methyl 3-aminocrotonate in 5 ml of isopropyl alcohol was treated and worked up as described in Example 1 to give 480 mg of methyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate as a yellow oil. Crystallization from ethyl acetate-petroleum benzin yielded yellow crystals, m.p. 127°–128° C.

EXAMPLE 17

A solution of 8.0 g of 5-acetonyl-3-chloromethyl-1,2,4-oxadiazole, 6.92 g of 3-nitrobenzaldehyde and 5.27 g of methyl 3-aminocrotonate in 20 ml of isopropyl alcohol was heated under reflux for 6 hours. After ice-cooling, the precipitated solid was collected by filtration, washed with cold isopropyl alcohol and dried to give 11.8 g of methyl 1,4-dihydro-2,6-dimethyl-3-(3-chloromethyl-1,2,4-oxadiazol-5-yl)-4-(3-nitrophenyl)-pyridine-5-carboxylate as yellow crystals, m.p. 200.5°–201.5° C.

A stirred solution of 1.0 g of the oxadiazolylpyridine prepared above, 0.60 g of N-methylbenzylamine and 0.50 g of triethylamine in DMF was allowed to stand at room temperature overnight. The reaction mixture was poured into ice-water and the resultant mixture was extracted with ethyl acetate. The extracts were washed with water, dried over magnesium sulfate and concentrated in vacuo. The residue was chromatographed on silica gel using chloroform-methanol (20:1, v/v) as eluent to give 1.30 g of methyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate as a yellow oil. Treatment of a solution of this base in ether with etherial hydrogen chloride afforded 1.18 g of the hydrochloride salt as yellow amorphous solid, m.p. 130° C. (decomp.).

EXAMPLES 18 TO 31

According to substantially the same procedure as that described in Example 17 with the exception of using the corresponding benzaldehydes instead of 3-nitrobenzaldehyde, there were obtained the following oxadiazolylpyridine derivatives as listed in Table III.

TABLE III

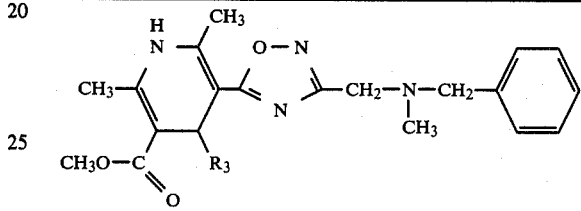

| Example | R₃ | Physical Data |
|---|---|---|
| 18 | 2-nitrophenyl | IR $\nu_{max}^{neat}$ cm⁻¹: 3320, 2950, 1700, 1650, 1530, 1495 |
| 19 | phenyl | IR $\nu_{max}^{neat}$ cm⁻¹: 3310, 1660, 1540, 1490, 1225 |
| 20 | 3-fluorophenyl | IR $\nu_{max}^{neat}$ cm⁻¹: 3310, 1655, 1540, 1480, 1220 |
| 21 | 2-fluorophenyl | IR $\nu_{max}^{neat}$ cm⁻¹: 3320, 1680, 1650, 1580, 1540 |
| 22 | 4-fluorophenyl | IR $\nu_{max}^{neat}$ cm⁻¹: 3310, 1650, 1540, 1490, 1225 |
| 23 | 3-chlorophenyl | IR $\nu_{max}^{neat}$ cm⁻¹: 3330, 1690, 1660, 1500, 1230 |
| 24 | 3-bromophenyl | IR $\nu_{max}^{neat}$ cm⁻¹: 3300, 1660, 1540, 1490, 1225 |
| 25 | 2,3-dichlorophenyl | IR $\nu_{max}^{neat}$ cm⁻¹: 3310, 1680, 1650, 1540, 1490, 1225 |
| 26 | 3-tolyl | IR $\nu_{max}^{neat}$ cm⁻¹: 3300, 1660, 1540, 1490, 1220 |
| 27 | 3,4-dimethoxyphenyl | IR $\nu_{max}^{neat}$ cm⁻¹: 3325, 1680, 1650, 1540, 1490, 1380 |
| 28 | 2,3-dimethoxyphenyl | m.p. 139–140° C. |
| 29 | 2-(2,2,2-trifluoro-ethoxy)phenyl | IR $\nu_{max}^{neat}$ cm⁻¹: 3330, 1690, 1655, 1545, 1490, 1280 |
| 30 | 2-benzyloxyphenyl | IR $\nu_{max}^{neat}$ cm⁻¹: 3300, 1690, 1645, 1535, 1485, 1220 |
| 31 | benzhydryl | IR $\nu_{max}^{neat}$ cm⁻¹: 3310, 1680, 1640, 1540, 1485 |

EXAMPLE 32

A solution of 500 mg of methyl 1,4-dihydro-2,6-dimethyl-3-(3-chloromethyl-1,2,4-oxadiazol-5-yl)-4-(3-nitrophenyl)pyridine-5-carboxylate, 445 mg of N-methyl-3,4-dimethoxybenzylamine and 250 mg of triethylamine in 5 ml of DMF was stirred at room temperature overnight. The reaction mixture was poured into ice-water and the resultant mixture was extracted with ether. The extracts were washed with water, dried over magnesium sulfate and concentrated in vacuo. The residue was chromatographed on silica gel using chloroform-methanol (50:1, v/v) as eluent to give 630 mg of methyl, 1,4-dihydro-2,6-dimethyl-3-[3-(N-3,4-dimethoxybenzyl-N-methylamino)methyl-1,2,4-oxadiazol-5- yl]-4-(3-nitrophenyl)pyridine-5-carboxylate, IR $\nu_{max}^{neat}$ cm$^{-1}$: 3320, 3180, 1680, 1645, 1520, 1490, 1220.

EXAMPLES 33 TO 73

According to substantially the same procedure as that described in Example 32 with the exception of using the corresponding amines instead of N-methyl-3,4-dimethoxybenzylamine, there were obtained the following oxadiazolylpyridine derivatives as listed in Table IV.

TABLE IV

[Structure: 1,4-dihydropyridine core with CH$_3$ groups, NH, CH$_3$O-C(=O)-, 3-nitrophenyl at 4-position, and an oxadiazole ring bearing -CH$_2$-X-T$_2$-R$_2$ substituent]

| Example | X—T$_2$—R$_2$ | IR $\nu_{max}$ cm$^{-1}$ |
|---|---|---|
| 33 | —N(CH$_3$)—CH$_2$—C$_6$H$_3$(OCH$_2$O) (3,4-methylenedioxyphenyl) | neat: 3300, 3225, 1680, 1650, 1525, 1490 |
| 34 | —N(CH$_3$)—CH$_2$—C$_6$H$_4$—F·HCl | Nujol: 3180, 2500–2450, 1700–1675, 1640 |
| 35 | —N(CH$_3$)—CH$_2$—C$_6$H$_4$—CH$_3$·HCl | Nujol: 3200, 1690, 1650, 1530, 1495, 1355 |
| 36 | —N(CH$_3$)—CH$_2$—C$_6$H$_3$(Cl)(Cl)·HCl (3,4-dichlorophenyl) | Nujol: 3200, 1680, 1640, 1590, 1490, 1350 |
| 37 | —N(CH$_3$)—CH$_2$—C$_6$H$_4$—CF$_3$ | neat: 3325, 1690, 1660, 1530, 1490, 1350 |
| 38 | —N(CH$_3$)—CH$_2$—C$_6$H$_4$—SO$_3$CH$_3$ | neat: 3320, 1700, 1680, 1650, 1520, 1490 |
| 39 | —N(CH$_2$CH$_3$)—CH$_2$—C$_6$H$_5$ | neat: 3320, 1700, 1680, 1650, 1520, 1490 |
| 40 | —N(CH(CH$_3$)$_2$)—CH$_2$—C$_6$H$_5$ | neat: 3320, 1690, 1530, 1500, 1355, 1235 |

TABLE IV-continued

[Structure: 1,4-dihydropyridine with H-N, CH₃ groups, CH₃O-C(=O)-, 3-nitrophenyl, and oxadiazole-CH₂-X-T₂-R₂ substituent]

| Example | X—T₂—R₂ | |
|---|---|---|
| 41 | −N(cyclopentyl)−CH₂−C₆H₅ | neat: 3320, 2950, 1700, 1680, 1655, 1525 |
| 42 | −N(−CH₂−C₆H₅)₂·HCl | Nujol: 1690, 1640, 1580, 1520, 1490, 1340 |
| 43 | −N(CH₃)−CH₂CH₂−C₆H₅ | neat: 3320, 2950, 1680, 1650, 1525, 1490 |
| 44 | −N(CH₃)−CH₂CH₂CH₂−C₆H₅·HCl | Nujol: 3150, 1675, 1635, 1515, 1480, 1340 |
| 45 | −N(CH₃)−CH₂CH₂−(3,4-methylenedioxyphenyl) | neat: 3340, 3020, 2950, 1690, 1650, 1510 |
| 46 | −NH−CH(CH₃)−C₆H₅ | neat: 3320, 1690, 1655, 1525, 1490, 1350 |
| 47 | −NH−C(CH₃)₂−C₆H₅ | neat: 3320, 2980, 1690, 1655, 1525, 1490 |
| 48 | −NH−CH(−C₆H₄−OCH₃)₂ | neat: 3320, 1680, 1650, 1520, 1490, 1350 |
| 49 | −NH−CH₂CH₂−(3,4-dimethoxyphenyl) | neat: 3325, 1690, 1655, 1520, 1510 |
| 50 | −NH−CH₂CH₂O−(2-methoxyphenyl) | neat: 3325, 1690, 1655, 1530, 1500 |

TABLE IV-continued

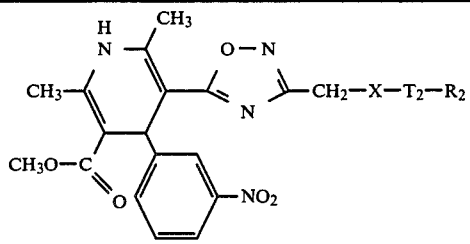

| Example | X—T$_2$—R$_2$ | |
|---|---|---|
| 51 | —NH—CH(CH$_3$)CH$_2$CH$_2$—C$_6$H$_5$ | neat: 3325, 1690, 1655, 1520, 1510 |
| 52 | —NH—CH(CH$_3$)CH$_2$CH$_2$—(3-ethoxy-4-hydroxyphenyl)·HCl | Nujol: 3150, 1670, 1640, 1520, 1480, 1340 |
| 53 | —NH—CH(CH$_3$)CH$_2$CH$_2$—(4-hydroxyphenyl) | neat: 3300, 1680, 1650, 1610, 1515, 1485 |
| 54 | —N(CH$_3$)—CH$_2$CH$_2$—N(piperazinyl)-(2-methoxyphenyl) | neat: 3300, 1695, 1645, 1520, 1495 |
| 55 | —N(piperazinyl)—phenyl | neat: 3320, 1700, 1655, 1600, 1530, 1495 |
| 56 | —N(piperazinyl)—(2-methoxyphenyl) | neat: 3310, 2950, 2830, 1700, 1650, 1520 |
| 57 | —N(piperazinyl)—(3-trifluoromethylphenyl) | neat: 3320, 1700, 1680, 1650, 1605, 1520 |
| 58 | —N(piperazinyl)—(2-pyrimidinyl)·2HCl | Nujol: 1680, 1620, 1580, 1520, 1490, 1340 |
| 59 | —N(piperazinyl)—CH(C$_6$H$_5$)$_2$ | Nujol: 3300, 1700, 1680, 1650, 1525 |
| 60 | —N(piperazinyl)—CH$_2$—(3,4,5-trimethoxyphenyl)·HCl | Nujol: 1690, 1650, 1600, 1500, 1350 |

TABLE IV-continued

| Example | X—T₂—R₂ | Physical Data |
|---|---|---|
| 61 | —N(piperazine)N—CO-adamantyl | neat: 3300, 3220, 1690, 1600, 1525, 1495 |
| 62 | —N(piperazine)N—CH₂-adamantyl | IR $\nu_{max}^{neat}$ cm⁻¹: 3290, 3200, 1680, 1650, 1595, 1520 |
| 63 | —N(piperidine)-phenyl | IR $\nu_{max}^{neat}$ cm⁻¹: 3300, 1700, 1650, 1520, 1480, 1340 |
| 64 | —N(piperidine)-CO-(4-F-phenyl) | IR $\nu_{max}^{neat}$ cm⁻¹: 3320, 1675, 1600, 1525, 1490 |
| 65 | —N(piperidine) | IR $\nu_{max}^{neat}$ cm⁻¹: 3300, 2950, 1690, 1650, 1520, 1490 |
| 66 | —N(pyrrolidine, N-CH₃)-phenyl | IR $\nu_{max}^{neat}$ cm⁻¹: 3330, 2800, 1690, 1660, 1530, 1490 |
| 67 | —N(isoindoline) | IR $\nu_{max}^{neat}$ cm⁻¹: 3300, 1680, 1650, 1520, 1490, 1350 |
| 68 | —N(tetrahydroisoquinoline)·HCl | IR $\nu_{max}^{neat}$ cm⁻¹: 3180, 1675, 1640, 1520, 1490, 1350 |
| 69 | —N(CH₂)₇ (azocane) | m.p. 159° C. (decomp.) |
| 70 | —N(CH₃)-cyclohexyl | IR $\nu_{max}^{neat}$ cm⁻¹: 3170, 1700, 1645, 1530, 1490 |
| 71 | —N(CH₃)—CH₂-(3-pyridyl) | IR $\nu_{max}^{neat}$ cm⁻¹: 3300, 3200, 1700, 1680, 1650, 1525 |

TABLE IV-continued

[Structure: 1,4-dihydropyridine with CH3, NH, CH3 on pyridine ring; CH3O-C(=O) ester; 3-nitrophenyl group; and 1,2,4-oxadiazole substituent bearing -CH2-X-T2-R2]

| Example | X—T2—R2 | IR |
|---|---|---|
| 72 | —N(CH3)—CH2—(2-furyl) | IR $\nu_{max}^{neat}$ cm$^{-1}$: 3330, 1690, 1660, 1530, 1500, 1350 |
| 73 | —N(CH3)—CH2—(2-thienyl) | IR $\nu_{max}^{neat}$ cm$^{-1}$: 3320, 1700, 1680, 1650, 1520, 1480 |

EXAMPLE 74

A mixture of 530 mg of 5-acetonyl-3-chloromethyl-1,2,4-oxadiazole, 450 mg of 3-nitrobenzaldehyde and 560 mg of 2-(n-propoxy)ethyl 3-aminocrotonate in 3 ml of isopropyl alcohol was heated under reflux for 8 hours. The reaction mixture was concentrated in vacuo and the residue was chromatographed on silica gel using benzene-acetonitrile (10:1) as eluent to give 1.35 g of 2-(n-propoxy)ethyl 1,4-dihydro-2,6-dimethyl-3-(3-chloromethyl-1,2,4-oxadiazol-5-yl)-4-(3-nitrophenyl)-pyridine-5-carboxylate. Recrystallization from n-hexane-isopropylalcohol afforded pale yellow crystals, m.p. 129°–130° C.

A solution of 480 mg of the oxadiazolylpyridine prepared above, 240 mg of N-methylbenzylamine and 200 mg of triethylamine in 10 ml of dioxane was heated at 90°–95° C. with stirring for 18 hours. The reaction mixture was concentrated in vacuo and the residue was chromatographed on silica gel using benzeneacetonitrile (10:1) as eluent to give 470 mg of 2-(n-propoxy)ethyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate as pale yellow resin. Treatment of a solution of this base in ether with etherial hydrogen chloride afforded 460 mg of the hydrochloride salt as pale yellow amorphous solid, IR $\nu_{max}^{Nujol}$ cm$^{-1}$: 3180, 1685, 1645, 1525, 1490, 1350.

EXAMPLES 75 TO 84

According to substantially the same procedure as that described in Example 74 with the exception of using the corresponding 3-aminocrotonates instead of n-propoxyethyl 3-aminocrotonate, there were obtained the following oxadiazolylpyridine derivatives as listed in Table V.

TABLE V

[Structure: 1,4-dihydropyridine with R8O-C(=O) ester, 3-nitrophenyl group, and 1,2,4-oxadiazole bearing -CH2-N(CH3)-CH2-phenyl·(HCl)n]

| Example | R8 | n | IR $\nu_{max}$ cm$^{-1}$ |
|---|---|---|---|
| 75 | —CH2CH3 | 0 | neat: 3320, 2980, 1700, 1680, 1650, 1580 |
| 76 | —CH(CH3)2 | 1 | Nujol: 3180, 1690, 1645, 1530, 1495 |
| 77 | —(CH2)7CH3 | 0 | Nulol: 3200, 1680, 1650, 1530, 1495, 1350 |
| 78 | —CH2CH2CN | 0 | Nujol: 3180, 2250, 1700, 1680, 1640, 1520 |
| 79 | —CH2CH2OCH3 | 1 | Nujol: 3170, 1685, 1645, 1530, 1490, 1350 |
| 80 | —CH2CH2OC(CH3)3 | 1 | Nujol: 3200, 1680, 1645, 1530, 1490, 1350 |
| 81 | —CH2CH=C(CH3)2 | 0 | neat: 3320 3240, 1700, 1655, 1525, 1490 |
| 82 | —CH2-cyclopropyl | 0 | neat: 3300, 3230, 1700, 1650, 1520, 1490 |
| 83 | —CH2-(2-pyridyl) | 0 | neat: 3300, 1680, 1650, 1520, 1490, 1345 |
| 84 | —CH2-(3-pyridyl) | 0 | neat: 3300, 3200, 1700, 1650, 1520, 1495 |

EXAMPLE 85

A stirred solution of 500 mg of 5-acetonyl-3-chloromethyl-1,2,4-oxadiazole, 390 mg of 3-fluorobenzaldehyde and 362 mg of methyl 3-aminocrotonate in 20 ml of isopropyl alcohol was heated under reflux for 5 hours. The reaction mixture was concentrated in vacuo and the residue was chromatographed on silica gel using chloroform as eluent to give 780 mg of methyl 1,4-dihydro-2,6-dimethyl-3-(chloromethyl-1,2,4-oxadiazol-5-yl)-4-(3-fluorophenyl)pyridine-5-carboxylate. Recrystallization from ethyl acetate-isopropyl ether afforded pale yellow crystals, m,p, 186° C.

A stirred solution of 500 mg of the oxadiazolylpyridine prepared above, 436 mg of N-methyl-3,4-methylenedioxybenzylamine and 267 mg of triethylamine in 3 ml of DMF was allowed to stand at room temperature overnight. The reaction mixture was then poured into ice-water and the resultant mixture was extracted with ethyl acetate. The extracts were washed with water, dried and evaporated in vacuo. The residue was chromatographed on silica gel using chloroform-methanol (50:1) as eluent to five 480 mg of methyl 1,4-dihydro-2,6-dimethyl-3-[3-[N-methyl-N-(3,4-methylenedioxybenzyl)amino]methyl-1,2,4-oxadiazol-5-yl]-4-(3-fluorofenyl)pyridine-5-carboxylate, IR $v_{max}^{neat}$ cm$^{-1}$: 3300, 1660, 1540, 1480, 1435, 1380, 1235.

EXAMPLES 86 TO 89

According to substantially the same procedure as that described in Example 85 with the exception of using the corresponding amines instead of N-methyl-3,4-methylenedioxybenzylamine, there were obtained the following oxadiazolylpyridine derivatives as listed in Table VI.

TABLE VI

| Example | X—T$_2$—R$_2$ | IR $v_{max}^{neat}$ cm$^{-1}$ |
|---|---|---|
| 86 | —N(CH$_3$)—CH$_2$—(3-Cl-phenyl) | 3320, 3250, 1700, 1655, 1545, 1490 |
| 87 | —N(CH$_3$)—CH$_2$—(pyridyl) | 3300, 3190, 1680, 1640, 1490, 1220 |
| 88 | —NH—CH((4-OCH$_3$-phenyl)$_2$) | 3320, 1680, 1650, 1610, 1500, 1240 |
| 89 | —N(piperazinyl)N—CH((Cl)$_2$-phenyl) | 3320, 3020, 2950, 2820, 1690, 1655 |

EXAMPLE 90

To a cooled mixture of 2.8 g of 1-benzyl-1-methylhydroxyguanidine and 1.3 g of triethylamine in 30 ml of benzene was added dropwise 1.3 ml of diketene under nitrogen. The reaction mixture was stirred at room temperature for 2 hours and then concentrated in vacuo. After adding 50 ml of toluene to the residue, the resultant solution was heated under reflux for 4 hours with a water separator. The solvent was evaporated in vacuo and the residue was chromatographed on silica gel using chloroform-methanol (70:1) as eluent to give 1.7 g of 5-acetonyl-3-(N-benzyl-N-methylamino)-1,2,4-oxadiazole as a colorless oil, IR $v_{max}^{neat}$ cm$^{-1}$: 1725, 1590, 1410, 1355, 1155.

A stirred solution of 1.7 g of the oxadiazole prepared above, 1.0 g of 3-nitrobenzaldehyde and 790 mg of methyl 3-aminocrotonate in 4 ml of isopropyl alcohol was heated under reflux for 4 hours. The reaction mixture was concentrated in vacuo and the residue was chromatographed on silica gel using chloroform-methanol (70:1) as eluent to give 3.24 g of methyl 1,4-dihydro-2,6-dimethyl-3-[3-(N-benzyl-N-methylamino)-1,2,4-oxadiazol-5-yl]-4-(3-nitrophenyl)pyridine-5-carboxylate as a yellow oil. Crystallization from n-hexane-ethyl acetate gave yellow prisms, m.p. 182°–184° C.

EXAMPLE 91

According to substantially the same procedure as that described in Example 90 with the exception of using the corresponding amidoximes instead of 1-benzyl-1-methylhydroxyguanidine, these was obtained methyl 1,4-dihydro-2,6-dimethyl-3-[3-[4-(N-benzyl-N-methylamino)methylphenyl]-1,2,4-oxadiazol-5-yl]-4-(3-nitrophenyl)pyridine-5-carboxylate, m.p. 192°–193° C.

EXAMPLE 92

A stirred solution of 1.0 g of 5-acetonyl-3-chloromethyl-1,2,4-oxadiazole, 0.95 g of 3-nitrobenzaldehyde and 0.52 g of 3-aminocrotononitrile in 10 ml of isopropyl alcohol was heated under reflux for 4 hours and then concentrated in vacuo. The residue was chromatographed on silica gel using chloroform-methanol (40:1) as eluent to give 0.90 g of 1,4-dihydro-2,6-dimethyl-3-(3-chloromethyl-1,2,4-oxadiazol-5-yl)-4-(3-nitrophenyl)pyridine-5-carbonitrile, m.p. 204.5°–206.5° C.

A stirred solution of 500 mg of the oxadiazolylpyridine prepared above, 324 mg of N-methylbenzylamine and 270 mg of triethylamine in 2 ml of DMF was allowed to stand at room temprature for 7 hours. After addition of water, the resultant mixture was extracted with ethyl acetate. The extracts were washed with water, dried over magnesium sulfate and concentrated in vacuo. The residue was chromatographed on silica gel using chloroform-methanol (20:1) as eluent to give 496 mg of 1,4-dihydro-2,6-dimethyl-3-[3-(N-benzyl-N-methylamino)methyl-1,2,4-oxadiazol-5-yl]-4-(3-nitrophenyl)pyridine-5-carbonitrile as a resin, IR $v_{max}^{neat}$ cm$^{-1}$: 3300, 3230, 2200, 1660, 1520, 1500.

EXAMPLE 93

A stirred solution of 0.53 g of 5-acetonyl-3-chloromethyl-1,2,4-oxadiazole, 0.46 g of 3-nitrobenzaldehyde and 0.30 g of 2-amino-4-oxo-2-pentene in 4 ml of isopropyl alcohol was heated under reflux for 14 hours. The reaction mixture was concentrated in vacuo and the residue was chromatographed on silica gel using benzene-acetonitrile (15:1) as eluent to give 0.79 g of 5-acetyl-1,4-dihydro-2,6-dimethyl-3-(3-chloromethyl-1,2,4-oxadiazol-5-yl)-4-(3-nitrophenyl)pyridine.

A stirred solution of 0.43 g of the oxadiazolylpyridine prepared above, 0.24 g of N-methyl benzylamine and 0.20 g of triethylamine in 10 ml of dioxane was heated at 90°-95° C. for 18 hours. The reaction mixture was concentrated in vacuo and the residue was chromatographed on silica gel using benzeneacetonitrile (10:1) as eluent to give 0.36 g of 5-acetyl-1,4-dihydro-2,6-dimethyl-3-[3-(N-benzyl-N-methylamino)methyl-1,2,4-oxadiazol-5-yl]-4-(3-nitrophenyl)pyridine, m.p. 138°-139° C.

EXAMPLE 94

A mixture of 960 mg of 1-(3-nitrophenyl)-3-oxo-1-butene and 5 ml of liquid ammonia in a sealed tube was allowed to stand at room temperature for 3 hours. After evaporation of ammonia, to the residue were added 870 mg of 5-acetonyl-3-chloromethyl-1,2,4-oxadiazole and 5 ml of isopropyl alcohol. The resultant mixture was heated under reflux for 2 hours and then concentrated in vacuo. The residue was chromatographed on silica gel using benzeneacetonitrile (15:1) as eluent to give 190 mg of 1,4-dihydro-2,6-dimethyl-3-(3-chloromethyl-1,2,4-oxadiazol-5-yl)-4-(3-nitrophenyl)pyridine as yellow crystals.

A stirred solution of 190 mg of the oxadiazolylpyridine prepared above, 120 mg of N-methylbenzylamine and 120 mg of triethylamine in 1 ml of DMF was allowed to stand at room temperature for 16 hours. After addition of water, the reaction mixture was extracted with ether and the extracts were washed with water, dried and evaporated in vacuo. The residue was chromatographed on silica gel using chloroform-methanol (30:1) as eluent to give 190 mg of 1,4-dihydro-2,6-dimethyl-3-[3-(N-benzyl-N-methylamino)methyl-1,2,4-oxadiazol-5-yl]-4-(3-nitrophenyl)pyridine as a resin. IR$\nu_{max}^{neat}$ cm$^{-1}$: 3380, 3320, 1690, 1620, 1520, 1490, 1350.

EXAMPLE 95

To a solution of 8.50 g of cyanoacetic acid and 10.1 g of chloroacetamidoxime was added 20.6 g of N,N'-dicyclohexylcarbodiimide with ice-cooling. After stirring for 1 hour at room temperature, the reaction mixture was filtered and the filtrate was concentrated in vacuo. The residue was triturated with 20 ml of ethyl acetate and the insoluble material was filtered off and washed with ethyl acetate. The filtrate was then concentrated in vacuo and the residue was dissolved in 50 ml of toluene. The resultant solution was heated under reflux for 20 minutes with a water separator. After cooling and adding 50 ml of ethyl acetate, the solution was decanted and evaporated in vacuo. The residue was chromatographed on silica gel using chloroform-methanol (50:1) as eluent to give 8.18 g of 3-chloromethyl-5-cyanomethyl-1,2,4-oxadiazole as an oil.

A stirred solution of 8.0 g of the oxadiazole prepared above, 9.26 g of N-methylbenzylamine and 10.32 g of triethylamine in 50 ml of THF was allowed to stand at room temperature overnight. The reaction mixture was concentrated in vacuo and the residue was dissolved in ethyl acetate. The resultant solution was washed with water, dried and evaporated in vacuo. The residue was chromatographed on silica gel using benzeneethyl acetate (2:1) as eluent to give 5.56 g of 3-(N-benzyl-N-methylamino)methyl-5-cyanomethyl-1,2,4-oxadiazole as an oil.

Hydrogen chloride was then passed at −10°-0° C. into a solution of 1.0 g of the aminomethyloxadiazole prepared above in a mixture of 3 ml of dry ethanol and 20 ml of chloroform. The reaction mixture was allowed to stand at about 5° C. overnight and concentrated in vacuo. The residue was dissolved in 30 ml of dry ethanol and ammonia was passed into the stirred solution for 1.5 hours with ice-cooling. After stirring at room temperature overnight, the precipitated material was filtered off. The filtrate was then concentrated in vacuo to give 5-amidinomethyl-3-(N-benzyl-N-methylamino)methyl-1,2,4-oxadiazole as a brown oil.

A stirred mixture of all of the amidinomethyloxadiazole prepared above, 500 mg of methyl 2-(3-nitrobenzylideneacetoacetate and 5 ml of ethanol was heated under reflux for 8 hours and then concentrated in vacuo. The residue was chromatographed on silica gel using chloroform-methanol (25:1) as eluent. Recrystallization of the product from chloroformethanol gave 0.33 g of methyl 2-amino-1,4-dihydro-6-methyl-3-[3-(N-benzyl-N-methylamino)methyl-1,2,4-oxadiazol-5-yl]-4-(3-nitrophenyl)pyridine-5-carboxylate as yellow crystals, m.p. 206.5° C. (decomp.)

EXAMPLE 96

A stirred solution of 1.20 g of 5-acetonyl-3-chloromethyl-1,2,4-oxadiazole, 1.20 g of methyl 3-amino-4-dimethoxycrotonate and 1.04 g of 3-nitrobenzaldehyde in 5 ml of isopropyl alcohol was heated under reflux for 6 hours. The reaction mixture was concentrated in vacuo and the residue was chromatographed on silica gel using chloroform-methanol (50:1) as eluent to give 1.62 g of methyl 1,4-dihydro-6-dimethoxymethyl-3-(3-chloromethyl-1,2,4-oxadiazol-5-yl)-2-methyl-4-(3-nitrophenyl)pyridine-5-carboxylate as yellow crystals, m.p. 141°-142° C.

A stirred solution of 1.50 g of the oxadiazolylpyridine prepared above, 0.59 g of N-methylbenzylamine and 0.49 g of triethylamine in 5 ml of DMF was allowed to stand at room temperature for 23 hours. The reaction mixture was diluted with water and then extracted with ether. The extracts were washed with water, dried and evaporated in vacuo. The residue was chromatographed on silica gel using chloroform-methanol (30:1) as eluent to give 1.08 g of methyl 1,4-dihydro-6-dimethoxymethyl-3-[3-(N-benzyl-N-methylamino)methyl-1,2,4-oxadiazol-5-yl]-2-methyl-4-(3-nitrophenyl)pyridine-5-carboxylate, IR $\nu_{max}^{neat}$ cm$^{-1}$: 3380, 2830, 1700, 1655, 1620, 1525.

EXAMPLE 97

To a solution of 1.0 g of methyl 1,4-dihydro-6-dimethoxymethyl-3-[3-(N-benzyl-N-methylamino)methyl-1,2,4-oxadiazol-5-yl]-2-methyl-4-(3-nitrophenyl)pyridine-5-carboxylate in 15 ml of acetone was added 2 ml of 6N-hydrochloric acid. After stirring at room temperature for 3 hours, the reaction mixture was neutralized with sodium bicarbonate solution and then concentrated in vacuo. To the residue was added ethyl acetate and the resultant solution was washed with water, dried and evaporated in vacuo. The residue was chromatographed on silica gel using chloroform-methanol (50:1) as eluent to give 740 mg of methyl 1,4-dihydro-3-[3-(N-benzyl-N-methylamino)methyl-1,2,4-oxadiazol-5-yl]-6-formyl-2-methyl-4-(3-nitrophenyl)pyridine-5-carboxylate, IR $\nu_{max}^{neat}$ cm$^{-1}$: 3350, 1700, 1680, 1640, 1600, 1520.

To a stirred solution of 370 mg of the formylpyridine in 5 ml of ethanol was added 30 mg of sodium borohydride with ice-cooling. After sitrring for 1.5 hours, the reaction mixture was quenched by adding 2 ml of 1N-hydrochloric acid and then concentrated in vacuo. The residue was neutralized by adding sodium bicarbonate solution and the resultant solution was extracted with ether. The extracts were washed with water, dried and evaporated in vacuo. The residue was chromatographed on silica gel using chloroform-methanol (20:1) as eluent. Crystallization of the product from isopropyl ether gave 240 mg of methyl 1,4-dihydro-3-[3-(N-benzyl-N-methylamino)methyl-1,2,4-oxadiazol-5-yl]-6-hydroxymethyl-2-methyl-4-(3-nitrophenyl)pyridine-5-carboxylate as yellow crystals, m.p. 126.5°–128° C.

EXAMPLE 98

According to substantially the same procedure as that described in Example 96 with the exception of using methyl 3-amino-4-methoxycrotonate instead of methyl 3-amino-4-dimethoxycrotonate, there were obtained the following oxadiazolyl pyridines:
methyl 1,4-dihydro-3-(3-chloromethyl-1,2,4-oxadiazol-5-yl)-6-methoxymethyl-2-methyl-4-(3-nitrophenyl)-pyridine-5-carboxylate, m.p. 138°–139° C.
methyl 1,4-dihydro-3-[3-(N-benzyl-N-methylamino)-methyl-1,2,4-oxadiazol-5-yl]-6-methoxymethyl-2-methyl-4-(3-nitrophenyl)pyridine-5-carboxylate, IR $\nu_{max}^{neat}$ cm$^{-1}$: 3390, 1690, 1655, 1530, 1480, 1350, 1230.

EXAMPLE 99

To a stirred mixture of 1.21 g of 3-(N-benzyl-N-methylamino)methyl-5-cyanomethyl-1,2,4-oxadiazole prepared in Example 95 and 1.25 g of methyl 2-(3-nitrobenzylidene)acetoacetate in 10 ml of ethanol was added 0.1 ml of piperidine. The reaction mixture was heated under reflux for 3 hours and then concentrated in vacuo. The residue was triturated with 10 ml of ethyl acetate and the insoluble crystals were collected by filtration. Treatment of a solution of this base in chloroform with etherial hydrogen chloride afforded 820 mg of methyl 2-amino-3-[3-(N-benzyl-N-methylamino)-methyl-1,2,4-oxadiazol-5-yl]-6-methyl-4-(3-nitrophenyl)-4H-pyran-5-carboxylate as pale yellow powder, m.p. 201.5° C. (decomp.).

EXAMPLE 100

To a solution of 2.0 g of 3,3-ethylenedioxybutylamidoxime and 6.03 g of methyl N-benzyl-N-methylaminoacetate in 50 ml of toluene was added 6.04 g of 28% sodium methoxide solution in methanol. The reaction mixture was heated under reflux for 6 hours and then concentrated in vacuo. To the residue was added ethyl acetate and the resultant solution was washed with water, dried over magnesium sulfate and evaporated in vacuo. The residue was chromatographed on silica gel using benzene-ethyl acetate (5:1) as eluent to give 2.24 g of 5-(N-benzyl-N-methylamino)-methyl-3-(2,2-ethylenedioxy)propyl-1,2,4-oxadiazole as an oil.

A solution of all of the oxadiazole prepared above in a mixture of 40 ml of methanol and 4 ml of conc. hydrochloric acid was heated under reflux for 10 hours. The reaction mixture was concentrated in vacuo and the residue was neutralized with sodium bicarbonate solution and then extracted with ethyl acetate. The organic phase was washed with water, dried and evaporated in vacuo. The residue was chromatographed on silica gel using chloroform-metanol (30:1) as eluent to give 0.9 g of 5-(N-benzyl-N-methylamino)methyl-3-acetonyl-1,2,4-oxadiazole as an oil.

A stirred solution of 800 mg of acetonyloxadiazole, 470 mg of 3-nitrobenzaldehyde and 360 mg of methyl 3-aminocrotonate in 25 ml of isopropyl alcohol was heated under reflux for 26 hours. The mixture was concentrated in vacuo and the residue was chromatographed on silica gel using chloroform as eluent to give 720 mg of methyl 1,4-dihydro-2,6-dimethyl-3-[5-(N-benzyl-N-methylamino)methyl-1,2,4-oxadiazol-3-yl]-4-(3-nitrophenyl)pyridine-5-carboxylate, IR $\nu_{max}^{neat}$ cm$^{-1}$: 3300, 1660, 1620, 1580, 1520, 1490, 1345.

EXAMPLE 101

To a stirred solution of 16.2 g of triethyl orthoacetate in 8.3 g of pyridine was added dropwise 16.0 g of bromine during 1 hour with ice-cooling. After the reaction mixture was stirred at 10° C. for 3 hours, the precipitated materials was filtered off. The filtrate was concentrated in vacuo and the residue was distilled under reduced pressure to give 15.5 g of triethyl orthobromoacetate.

A stirred solution of 10.0 g of triethyl orthobromoacetate and 5.0 g of 3,3-ethylenedioxybutyrohydrazide in 50 ml of benzene was heated under reflux for 1 hour. The mixture was concentrated in vacuo and the residue was chromatographed on silica gel using chloroform-methanol (30:1) as eluent to give 3.92 g of 2-bromomethyl-5-(2,2-ethylenedioxy)propyl-1,3,4-oxadiazole as an oil.

A stirred solution of 2.0 g of the bromomethyl oxadiazole prepared above, 1.53 g of triethylamine and 1.84 g of N-methylbenzylamine in 10 ml of DMF was allowed to stand at room temperature for 65 hours. The reaction mixture was then diluted with water and extracted with ethyl acetate. The extracts were washed with water, dried over magnesium sulfate and evaporated in vacuo. The residue was chromatographed on silica gel using chloroform-methanol (20:1) as eluent to give 1.31 g of 2-(N-benzyl-N-methylamino)methyl-5-(2,2-ethylenedioxy)propyl-1,3,4-oxadiazole as an oil.

A solution of 1.10 g of the aminomethyloxadiazole prepared above in 5 ml of conc. hydrochloric acid and 5 ml of acetic acid was stirred in an ice bath for 5 hours and then raised to room temperature for 2 hours. The reaction mixture was neutralized by adding 1N-sodium hydroxide solution with ice-cooling and extracted with ethyl acetate. The extracts were washed with water, dried and evaporated in vacuo. The residue was chromatographed on silica gel using chloroform-methanol (20:1) as eluent to give 640 mg of 2-acetonyl-5-(N-benzyl-N-methylamino)-methyl-1,3,4-oxadiazole as an oil.

A stirred solution of 550 mg of the acetonyloxadiazole prepared above, 320 mg of 3-nitrobenzaldehyde and 242 mg of methyl 3-aminocrotonate in 10 ml of isopropyl alcohol was heated under reflux for 10 hours. The reaction mixture was concentrated in vacuo and the residue was chromatographed on silica gel using chloroform-methanol (10:1) as eluent to give 370 mg of methyl 1,4-dihydro-2,6-dimethyl-3-[2-(N-benzyl-N-methylamino)methyl-1,3,4-oxadiazol-5-yl]-4-(3-nitrophenyl)pyridine-5-carboxylate as an yellow oil, IR $\nu_{max}^{neat}$ cm $^{-1}$: 3300, 1650, 1515, 1340, 1220, 725.

EXAMPLE 102

To a solution of 3.0 g of chloroacetonitrile in 10 ml of dry ethanol was added 0.12 g of sodium methoxide. After the mixture was stirred at room temperature for 1 hour, there was added a solution of 2.28 g of 5-amino-3-methylisothiazole in 100 ml of dry methanol. The reaction mixture was heated under reflux for 6 hours and then concentrated in vacuo. The residue was chromatographed on alumina using ethyl acetate as eluent to give 3.32 g of 5-(2-amino-1-propenyl)-3-chloromethyl-1,2,4-thiadiazole.

A stirred solution of all of the thiadiazole prepared above and 4.36 g of methyl 2-(3-nitrobenzylidene)acetoacetate in 75 ml of isopropyl alcohol was heated under reflux for 6 hours. The mixture was then concentrated in vacuo and the residue was chromatographed on silica gel using chloroform-methanol (30:1) as eluent to give 3.16 g of methyl 1,4-dihydro-2,6-dimethyl-3-(3-chloromethyl-1,2,4-thiadiazol-5-yl)-4-(3-nitrophenyl)-pyridine-5-carboxylate, m.p. 205°–206° C.

According to the procedure described in Example 32, the thiadiazolyl pyridine prepared above was then reacted with the corresponding amine to give the following compounds:

Methyl 1,4-dihydro-2,6-dimethyl-3-[3-(N-benzyl-N-methylamino)methyl-1,2,4-thiadiazol-5-yl]-4-(3-nitrophenyl)pyridine-5-carboxylate, IR $\nu_{max}^{neat}$ cm$^{-1}$: 3300, 1665–1635, 1520, 1490–1470, 1345, 1230

Methyl 1,4-dihydro-2,6-dimethyl-3-[3-[4-(2-methoxyphenyl)-1-piperazinyl]methyl-1,2,4-thiadiazol-5-yl]-4-(3-nitrophenyl)pyridine-5-carboxylate, IR $\nu_{max}^{neat}$ cm$^{-1}$: 3300, 2810, 1680, 1635, 1520, 1490, 1340, 1230.

EXAMPLE 103

A stirred mixture of 343 mg of 5-(2-amino-1-propenyl)-3-chloromethyl-1,2,4-thiadiazole, 316 mg of 5-acetonyl-3-chloromethyl-1,2,4-oxadiazole and 273 mg of 3-nitrobenzaldehyde in 5 ml of isopropyl alcohol was heated under reflux for 10 hours. The mixture was concentrated in vacuo and the residue was chromatographed on silica gel using benzene-ethyl acetate (5:1) as eluent to give 134 mg of 1,4-dihydro-2,6-dimethyl-3-(3-chloromethyl-1,2,4-oxadiazol-5-yl)-5-(3-chloromethyl-1,2,4-thiadiazol-5-yl)-4-(3-nitrophenyl)pyridine.

A solution of 120 mg of the pyridine derivative prepared above, 100 mg of triethylamine and 120 mg of N-methylbenzylamine in 5 ml of DMF was stirred at room temperature for 24 hours. The reaction mixture was then poured into ice-water and the resultant mixture was extracted with ethyl acetate. The extracts were washed with water, dried and evaporated in vacuo. The residue was chromatographed on silica gel using chloroform-methanol (20:1) as eluent to give 100 mg of 1,4-dihydro-2,6-dimethyl-3-[3-(N-benzyl-N-methylamino)methyl-1,2,4-oxadiazol-5-yl]-5-[3-(N-benzyl-N-methylamino)methyl-1,2,4-thiadiazol-5-yl]-4-(3-nitrophenyl)pyridine, IR $\nu_{max}^{neat}$ cm$^{-1}$: 3280, 2810, 1640, 1520, 1490, 1260.

EXAMPLE 104

A mixture of 520 mg of 5-acetonyl-3-(N-benzyl-N-methylamino)methyl-1,2,4-oxadiazole, 150 mg of 3-nitrobenzaldehyde, 3 ml of isopropyl alcohol and 70 mg of 29% ammonia water in an autoclave was heated at 100° C. in an oil bath for 15 hours. After cooling, the mixture was evaporated in vacuo and the residue was chromatographed on silica gel using chloroform-methanol (30:1) as eluent to give 1,4-dihydro-2,6-dimethyl-3,5-di-[3-(N-benzyl-N-methylamino)methyl-1,2,4-oxadiazol-5-yl]-4-(3-nitrophenyl)pyridine, IR $\nu_{max}^{neat}$ cm$^{-1}$: 3300, 3000, 1655, 1525, 1490, 1450, 1350.

EXAMPLE 105

A mixture of 250 mg of methyl 2-(3-nitrobenzylidene)acetoacetate, 260 mg of 5-acetonyl-3-(N-benzyl-N-methylamino)methyl-1,2,4-oxadiazole, 3 ml of isopropyl alcohol and 40 mg of 29% ammonia water was reacted and worked up as described in Example 104 to give methyl 1,4-dihydro-2,6-dimetyl-3-[3-(N-benzyl-N-methylamino)methyl-1,2,4-oxadiazol-5-yl]-4-(3-nitrophenyl)pyridine-5-carboxylate, m.p. 126°–127° C.

EXAMPLE 106

To a stirred solution of 250 mg of methyl 1,4-dihydro-2,6-dimetyl-3-[3-(N-benzyl-N-methylamino)methyl-1,2,4-oxadiazol-5-yl]-4-(3-nitrophenyl)pyridine-5-carboxylate in 5 ml of dry DMF was added 24 mg of 60% sodium hydride with ice-cooling. After the mixture was stirred for 10 minutes, there was added 76 mg of methyl iodide. The reaction mixture was allowed to stand at room temperature for 6 hours, diluted by addition of ice-water and then extracted with ethyl acetate. The extracts were washed with water, dried and evaporated in vacuo. The residue was chromatographed on silica gel using chloroform-methanol (30:1) as eluent to give 190 mg of methyl 1,4-dihydro-3-[3-(N-benzyl-N-methylamino)methyl-1,2,4-oxadiazol-5-yl]-1,2,6-trimethyl-4-(3-nitrophenyl)pyridine-5-carboxylate, IR $\nu_{max}^{neat}$ cm$^{-1}$: 1690, 1635, 1580, 1520, 1340, 900.

EXAMPLE 107

To a stirred solution of 350 mg of 5-acetonyl-3-chloromethyl-1,2,4-oxadiazole in 10 ml of dry benzene-ether (3:1) was added dropwise with ice-cooling a solution of 190 mg of titanium tetrachloride in 1 ml of dry benzene. After the mixture was stirred for 1 hour, there was added dropwise 360 mg of n-propylamine with ice-cooling. The stirring was continued for 3 hours and then at room temperature for additional 3 hours. After the filtration of the reaction mixture, the filtrate was concentrated in vacuo. The residue was chromatographed on silica gel using benzene-acetonitrile (10:1) as eluent to give 5-[2-(n-propylamino)-1-propenyl]-3-chloromethyl-1,2,4-oxadiazole as an oil.

A stirred mixture of 100 mg of the oxadiazole prepared above, 115 mg of methyl 2-(3-nitrobenzylidene)acetoacetate and 3 ml of isopropyl alcohol was heated under reflux for 10 hours and then concentrated in vacuo. The residue was chromatographed on silica gel using benzene-acetonitrile (15:1) as eluent to give 180 mg of methyl 1,4-dihydro-2,6-dimethyl-3-(3-chloromethyl-1,2,4-oxadiazol-5-yl)-4-(3-nitrophenyl)-1-(n-propyl)pyridine-5-carboxylate.

A stirred mixture of all of the oxadiazolylpyridine prepared above, 100 mg of N-methylbenzylamine, 100 mg of triethylamine and 3 ml of dioxane was heated at 90° C. for 11 hours and then concentrated in vacuo. The residue was chromatographed on silica gel using benzene-acetonitrile (15:1) as eluent to give 150 mg of methyl 1,4-dihydro-2,6-dimethyl-3-[3-(N-benzyl-N-methylamino)methyl-1,2,4-oxadiazol-5-yl]-4-(3-nitrophenyl)-1-(n-propyl)pyridine-5-carboxylate, NMR (CDCl$_3$) δppm: 0.84 (triplet, 3H), 2.55 (singlet, 3H), 2.63 (singlet, 3H), 3.50–3.80 (multiplet, 6H), 5.30 (singlet, 1H), 7.17–7.47 (multiplet, 6H), 7.63–8.13 (multiplet, 3H).

EXAMPLE 108

According to substantially the same procedure as that of Example 74 with the exception of using ethyl 3-amino-2,6-heptadienoate instead of n-propoxyethyl 3-aminocrotonate, there was obtained ethyl 1,4-dihydro-6-(3-butenyl)-3-[3-(N-benzyl-N-methylamino)methyl-1,2,4-oxadiazol-5-yl]-2-methyl-4-(3-nitrophenyl)pyridine-5-carboxylate hydrochloride, IR $\nu_{max}^{Nujol}$ cm$^{-1}$: 3180, 3060, 1680, 1640, 1530, 1495, 1350.

EXAMPLE 109

According to substantially the same procedure as that of Example 74 with the exception of using ethyl 3-amino-4,4,4-trifluorocrotonate instead of n-propoxyethyl 3-aminocrotonate, there was obtained ethyl 1,4-dihydro-3-[3-N-benzyl-N-methylamino)methyl-1,2,4-oxadiazol-5-yl]-2-methyl-6-trifluoromethyl-4-(3-nitrophenyl)pyridine-5-carboxylate hydrochloride, IR $\nu_{max}^{Nujol}$ cm$^{-1}$: 3500–2700, 1735, 1620, 1530, 1350.

EXAMPLE 110

To a stirred solution of 1.06 g of 2-cyanoethyl 1,4-dihydro-2,6-dimetyl-3-[3-(N-benzyl-N-methylamino)-methyl-1,2,4-oxadiazol-5-yl]-4-(3-nitrophenyl)pyridine-5-carboxylate in 5 ml of ethylene glycol dimethyl ether was added a solution of 240 mg of sodium hydroxide in 10 ml of water. The reaction mixture was stirred at room temperature for 7 hours and then diluted by adding 5 ml of water. The mixture was washed with three 20 ml portions of methylene chloride and then acidified with dilute hydrochloric acid until the pH of the solution was about 1. The solution was decanted and the oily precipitate was dissolved in isopropyl alcohol. After the organic phase was concentrated in vacuo, the residue was chromatographed on silica gel using chloroform-isopropyl alcohol (10:1) as eluent to give 0.715 g of 1,4-dihydro-2,6-dimethyl-3-[3-(N-benzyl-N-methylamino)methyl-1,2,4-oxadiazol-5-yl]-4-(3-nitrophenyl)pyridine-5-carboxylic acid as an amorphous solid. Recrystallization from ethyl acetate-isopropyl ether gave colorless crystals, m.p. 171° C. (decomp.)

To a solution of 200 mg of the pyridine carboxylic acid prepared above in 2 ml of dry methylene chloride-DMF (4:1) was added 54 mg of thionyl chloride with ice-cooling. After then mixture was stirred for 1.5 hours, there was added 30 mg of methanol. The reaction mixture was allowed to stand at room temperature for 2 hours and the concentrated in vacuo. The solution of the residue in ethyl acetate was washed with water, dried over magnesium sulfate and evaporated in vacuo. The residue was chromatographed on silica gel using chloroform-methanol (20:1) as eluent to give 170 mg of methyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate as a yellow oil. Crystallization from ether afforded pale yellow fine crystals, m.p. 127°–128° C.

EXAMPLES 111 to 113

According to substantially the same procedure as that of Example 110 with the exception of using the corresponding alcohols instead of methanol, there were obtained the following oxadiazolylpyridine derivatives:

111. 2-Pyridylmethyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate, IR $\nu_{max}^{neat}$ cm$^{-1}$: 3300, 2930, 1680, 1650, 1520, 1490, 1345

112. 3-Pyridylmethyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate, IR $\nu_{max}^{Nujol}$ cm$^{-1}$: 3300, 3200, 1700, 1655, 1520, 1495, 1350

113. 2,2,2-Trifluoroethyl-1,4-dihydro-2,6-dimethyl-3-[3-(N-benzyl-N-methylamino)methyl-1,2,4-oxadiazol-5-yl]-4-(3-nitrophenyl)pyridine-5-carboxylate, m.p. 141.5°–142.5° C.

EXAMPLE 114

To a stirred mixture of 7.10 g of 2-cyanoethyl 1,4-dihydro-2,6-dimethyl-3-(3-chloromethyl-1,2,4-oxadiazol-5-yl)-4-(3-nitrophenyl)pyridine-5-carboxylate in 30 ml of ethylene glycohol dimethyl ether was added a solution of 1.92 g of sodium hydroxide in 50 ml of water. The reaction mixture was stirred at room temperature overnight and then diluted by adding 40 ml of water. The mixture was washed with methylene chloride and acidified with dilute hydrochloric acid until the pH of the solution was about 1. The precipitate was collected by filtration, washed with water and dried to give 6.1 g of 1,4-dihydro-2,6-dimetyl-3-(3-chloromethyl-1,2,4-oxadiazol-5-yl)-4-(3-nitrophenyl)pyridine-5-carboxylic acid as pale yellow powder, m.p. 196° C. (decomp.).

To a hot solution of 3.72 g of the racemic pyridinecarboxylic acid prepared above in 100 ml of dioxane was added a solution of 2.16 g of (S)-(−)-2-amino-1,1-diphenyl-1-propanol in 40 ml of dioxane. After the mixture was allowed to cool for 2.5 days, the precipitate were collected by filtration, washed with cold dioxane and dried to give 2.74 of the salt. It was recrystallized three times from dioxane and treated with 2N-hydrochloric acid. The free carboxylic acid was extracted with methylene chloride and the extracts were dried over magnesium sulfate and concentrated to dryness in vacuo to give 0.94 g of (+)-1,4-dihydro-2,6-dimethyl-3-(3-chloromethyl-1,2,4-oxadiazol-5-yl)-4-(3-nitrophenyl)-pyridine-5-carboxylic acid, m.p. 170° C. (decomp.), $[\alpha]_D^{25}$ +291° (c=0.07, CH$_3$OH).

According to the same optical resolution procedure as described above with the exception of using 1.62 g of the racemic pyridine carboxylic acid and 1.15 g of (R)-(+)-2-amino-1,1-diphenyl-1-propanol, there was obtained 0.35 g of (−)-1,4-dihydro-2,6-dimethyl-3-(3-chloromethyl-1,2,4-oxadiazol-5-yl)-4-(3-nitrophenyl)-pyridine-5-carboxylic acid, m.p. 170° C. (decomp.), $[\alpha]_D^{25}$ −278° (c=0.06, CH$_3$OH).

These enantiomers were respectively converted to the optically active methyl esters and then reacted with N-methylbenzylamine according to the procedure as described in Examples 110 and 32, respectively, to give (+)-methyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate, $[\alpha]_D^{25}$ +216° (c=0.11, CH$_3$OH), and (−)-methyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate, $[\alpha]_D^{25}$ −207° (c=0.11, CH$_3$OH).

EXAMPLE 115

According to substantially the same procedure as that described in Example 17 with the exception of using nicotinaldehyde instead of 3-nitrobenzaldehyde, there was obtained methyl 1,4-dihydro-2,6-dimethyl-3-(3-chloromethyl-1,2,4-oxadiazol-5-yl)-4-(3-pyridyl)pyridine-5-carboxylate, m.p. 234.5° C. (decomp.).

To a solution of 0.30 g of the pyridyl pyridine prepared above in 25 ml of methylene chloride was added 0.286 g of m-chloroperoxybenzoic acid. After the mixture was stirred at room temperature for 1.5 hour, the aqueous sodium bicarbonate was added and the stirring was continued overnight. The organic phase was separated, dried over magnesium sulfate and evaporated in vacuo. The residue was chromatographed on silica gel using chloroform-methanol (20:1) as eluent to give 0.16 g of 3-[1,4-dihydro-2,6-dimethyl-3-(3-chloromethyl-1,2,4-oxadiazol-5-yl)-5-methoxycarbonyl-4-pyridyl]-pyridine-N-oxide.

The pyridine-N-oxide was reacted with N-methyl-benzylamine as described in Example 17 to give 3-[1,4-dihydro-2,6-dimethyl-3-[3-N-benzyl-N-methylamino)-methyl-1,2,4-oxadiazol-5-yl]-5-methoxycarbonyl-4-pyridyl]pyridine-N-oxide, IR $\nu_{max}^{neat}$ cm$^{-1}$: 3300, 3200, 1700, 1650, 1500, 1230.

EXAMPLE 116

To a stirred solution of 1.0 g of methyl 1,4-dihydro-2,6-dimethyl-3-(3-chloromethyl-1,2,4-oxadiazol-5-yl)-4-(3-nitrophenyl)pyridine-5-carboxylate in 20 ml of THF was added 370 mg of benzyl mercaptan and 2 ml of 2N-sodium hydroxide solution. The mixture was stirred at room temperature for 1 hour and then concentrated in vacuo. The residue was chromatographed on silica gel using chloroform-methanol (30:1) as eluent and the separated product was crystalized from ether to give 1.09 g of methyl 1,4-dihydro-2,6-dietmyl-3-(3-benzylthiomethyl-1,2,4-oxadiazol-5-yl)-4-(3-nitrophenyl)pyridine-5-carboxylate, m.p. 168°-169° C.

EXAMPLE 117

To a solution of 1.00 g of methyl 1,4-dihydro-2,6-dimethyl-3-(3-benzylthiomethyl-1,2,4-oxadiazol-5-yl)-4-(3-nitrophenyl)pyridine-5-carboxylate in 50 ml of chloroform was added 0.47 g of m-chloroperoxybenzoic acid. After the mixture was stirred at room temperature for 3 hours, the aqueous sodium bicarbonate was added and the stirring was continued for a while. The chloroform layer was separated, washed, dried over magnesium sulfate and evaporated in vacuo. The residue was chromatographed on silica gel using chloroform-methanol (30:1) as eluent to give 980 mg of methyl 1,4-dihydro-2,6-dimethyl-3-(3-benzylsulfinylmethyl-1,2,4-oxadiazol-5-yl)-4-(3-nitrophenyl)pyridine-5-carboxylate, IR $\nu_{max}^{neat}$ cm$^{-1}$: 3290, 3210, 1680, 1645, 1520, 1490, 1230.

EXAMPLE 118

To a solution of 550 mg of methyl 1,4-dihydro-2,6-dimethyl-3-(3-benzylsulfinylmethyl-1,2,4-oxadiazol-5-yl)-4-(3-nitrophenyl)pyridine-5-carboxylate in 30 ml of chloroform was added 520 mg of m-chloroperoxybenzoic acid. After stirring at room temperature for 8 hours, the mixture was treated in the same manner as described in Example 117 to give 180 mg of methyl 1,4-dihydro-2,6-dimethyl-3-(3-benzylsulfonylmethyl-1,2,4-oxadiazol-5-yl)-4-(3-nitrophenyl)pyridine-5-carboxylate, m.p. 227° C.

What is claimed is:

1. A compound of the formula,

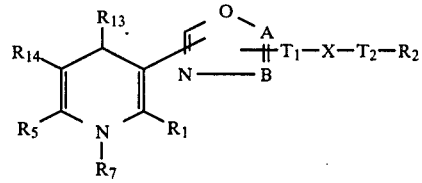

or a pharmaceutically acceptable acid addition salt thereof wherein A is nitrogen and B is CH; $T_1$ is lower alkylene or lower alkenylene each unsubstituted or substituted by phenylene; or $T_1$ is a single bond; X is

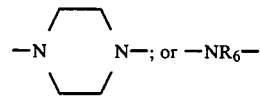

wherein
$R_6$ is hydrogen, lower alkyl, lower cycloalkyl or benzyl;
$T_2$ is carbonyl, lower alkylene unsubstituted or substituted by phenyl which in turn is unsubstituted or substituted by lower alkyl or halogen; or $T_2$ is a single bond; $R_2$ is phenyl or phenoxy each unsubstituted or substituted by one or more of the same or different substituents selected from the group consisting of halogen, trifluoromethyl, cyano, lower alkyl, lower alkoxy, methylenedioxy, lower alkylsulfonyl or hydroxy; or $R_2$ is pyridyl, pyrimidinyl, furyl, thienyl, lower cycloalkyl or adamantyl; or when X is —NR$_6$—, $R_2$ and $R_6$ taken together with the nitrogen to which they are attached form pyrrolidinyl, piperidinyl or azacyclooctanyl each unsubstituted or substituted by o-phenylene which in turn is unsubstituted or substituted by phenyl, benzoyl, mono- or dihalophenyl, or mono- or dihalobenzoyl; $R_{13}$ is phenyl unsubstituted or substituted by one or more of the same or different substituents selected from the group consisting of halogen, nitro, trifluoromethyl, cyano, lower alkyl, lower alkoxy, polyfluoro-lower alkoxy or benzyloxy; $R_{14}$ is COOR$_8$ wherein R$_8$ is a saturated or unsaturated $C_1$-$C_{10}$ hydrocarbon radical; or $R_{14}$ is —T$_3$R$_9$ wherein T$_3$ is lower alkylene and R$_9$ is lower alkoxy, lower cycloalkyl, cyano, polyfluoro-lower alkyl or pyridyl; $R_1$ and $R_5$ are each lower alkyl or lower alkenyl; $R_7$ is hydrogen.

2. A compound according to claim 1, wherein $T_1$ is lower alkylene; $R_2$ is phenyl unsubstituted or substituted by one or more of the same or different substituents selected from the group consisting of halogen, trifluoromethyl, cyano, lower alkyl, lower alkoxy, methylenedioxy, lower alkylsulfonyl or hydroxy; or $R_2$ is pyridyl, furyl or thienyl; $T_2$ is lower alkylene or a single bond; $R_1$ and $R_5$ are each lower alkyl; $R_6$ is hydrogen, lower alkyl or benzyl; $R_8$ is a saturated $C_{1-10}$ hydrocarbon radical; or $R_{14}$ is —T$_3$—R$_9$, wherein R$_9$ is lower cycloalkyl or pyridyl.

3. A compound according to claim 2, wherein $T_1$ is methylene; $R_6$ is hydrogen or lower alkyl; $R_2$ is phenyl unsubstituted or substituted by one or more of the same or different substituents selected from the group consisting of halogen, trifluoromethyl, cyano, lower alkyl, lower alkoxy, methylenedioxy, lower alkylsulfonyl or hydroxy; or $R_2$ is pyridyl; or when X is —NR$_6$—, $R_2$ and $R_6$ taken together with the nitrogen to which they are attached form piperidinyl unsubstituted or substituted with benzoyl or mono- or dihalobenzoyl; and $R_1$ and $R_5$ are methyl.

4. A compound according to claim 3, wherein; $R_6$ is hydrogen or methyl; $R_8$ is $C_{1-4}$ alkyl or picolyl.

5. A compound of the formula,

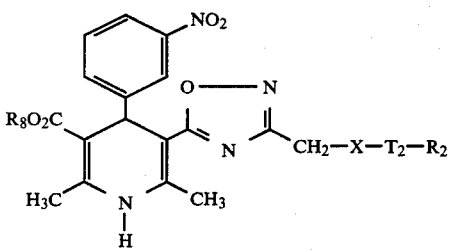

or a pharmaceutically acceptable acid addition salt thereof wherein X, $T_2$, $R_2$ and $R_8$ are as defined in claim 4.

6. The compound according to claim 4, which is methyl 1,4-dihydro-2,6-dimethyl-3-(3-piperidinomethyl-1,2,4-oxadiazol-5-yl)-4-phenylpyridine-5-carboxylate.

7. The compound according to claim 4, which is methyl 1,4-dihydro-2,6-dimethyl-3-(3-piperidinomethyl-1,2,4-oxadiazol-5-yl)-4-(3-nitrophenyl)pyridine-5-carboxylate.

8. The compound according to claim 4, which is methyl 1,4-dihydro-2,6-dimethyl-3-(3-piperidinomethyl-1,2,4-oxadiazol-5-yl)-4-(3,4-dichlorophenyl)pyridine-5-carboxylate.

9. The compound according to claim 4, which is methyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate.

10. The compound according to claim 4, which is methyl 1,4-dihydro-2,6-dimethyl-[3-(N-benzyl-N-methylamino)methyl-1,2,4-oxadiazol-5-yl]-4-(3-fluorophenyl)pyridin-5-carboxylate.

11. The compound according to claim 4, which is methyl 1,4-dihydro-2,6-dimethyl-[3-(N-benzyl-N-methylamino)methyl-1,2,4-oxadiazol-5-yl]-4-(2,3-dichlorophenyl)pyridine-5-carboxylate.

12. The compound according to claim 4, which is methyl 1,4-dihydro-2,6-dimethyl-3-[N-(4-methylbenzyl)-N-methylamino]methyl-1,2,4-oxadiazol-5-yl]-4-(3-nitrophenyl)pyridine-5-carboxylate.

13. The compound according to claim 4, which is methyl 1,4-dihydro-2,6-dimethyl-3-[N-(4-methoxybenzyl)-N-methylamino]methyl-1,2,4-oxadiazol-5-yl]-4-(3-nitrophenyl)pyridine-5-carboxylate.

14. The compound according to claim 4, which is methyl 1,4-dihydro-2,6-dimethyl-3-[3-(N-methyl-N-phenethylamino)methyl-1,2,4-oxadiazol-5-yl]-4-(3-nitrophenyl)pyridine-5-carboxylate.

15. The compound according to claim 4, which is methyl 1,4-dihydro-2,6-dimethyl-3-[3-[N-methyl-N-(3-phenylpropyl)amino]methyl-1,2,4-oxadiazol-5-yl]-4-(3-nitrophenyl)pyridine-5-carboxylate.

16. The compound according to claim 4, which is methyl 1,4-dihydro-2,6-dimethyl-3-[3-[N-methyl-N-(3,4-dimethoxyphenyl)ethylamino]methyl-1,2,4-oxadiazol-5-yl]-4-(3-nitrophenyl)pyridine-5-carboxylate.

17. The compound according to claim 4, which is methyl 1,4-dihydro-2,6-dimethyl-3-[3-[N-methyl-N-(3-pyridyl)methylamino]methyl-1,2,4-oxadiazol-5-yl]-4-(3-nitrophenyl)pyridine-5-carboxylate.

18. The compound according to claim 4, which is methyl 1,4-dihydro-2,6-dimethyl-3-[3-[4-(2-methoxyphenyl)-1-piperazinyl]methyl-1,2,4-oxadiazol-5-yl]-4-(3-nitrophenyl)pyridine-5-carboxylate.

19. The compound according to claim 4, which is methyl 1,4-dihydro-2,6-dimethyl-3-[3-[4-(3-trifluoromethylphenyl)-1-piperazinyl]methyl-1,2,4-oxadiazol-5-yl]-4-(3-nitrophenyl)pyridine-5-carboxylate.

20. The compound according to claim 4, which is methyl 1,4-dihydro-2,6-dimethyl-3-[5-(N-benzyl-N-methylamino)methyl-1,2,4-oxadiazol-3-yl]-4-(3-nitrophenyl)pyridine-5-carboxylate.

21. The compound according to claim 4, which is methyl 1,4-dihydro-2,6-dimethyl-3-[2-(N-benzyl-N-methylamino)methyl-1,3,4-oxadiazol-5-yl]-4-(3-nitrophenyl)pyridine-5-carboxylate.

22. The compound according to claim 3, which is methyl 1,4-dihydro-2,6-dimethyl-3-[3-(N-benzyl-N-ethylamino)methyl-1,2,4-oxadiazol-5-yl]-4-(3-nitrophenyl)pyridine-5-carboxylate.

23. The compound according to claim 3, which is methyl 1,4-dihydro-2,6-dimethyl-3-[3-(N-benzyl-N-isopropylamino)methyl-1,2,4-oxadiazol-5-yl]-4-(3-nitrophenyl)pyridine-5-carboxylate.

24. The compound according to claim 3, which is ethyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate.

25. The compound according to claim 3, which is isopropyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate.

26. The compound according to claim 3, which is 2-methoxyethyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate.

27. The compound according to claim 3, which is cyclopropylmethyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate.

28. The compound according to claim 3, which is 2-pyridylmethyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate.

29. The compound according to claim 3, which is 3-pyridylmethyl 1,4-dihydro-2,6-dimethyl-3-[3-(N-benzyl-N-methylamino)methyl-1,2,4-oxadiazol-5-yl]-4-(3-nitrophenyl)pyridine-5-carboxylate.

30. The compound according to claim 3, which is methyl 1,4-dihydro-2,6-dimethyl-3-[3-[2-(N-benzyl-N-methylamino)ethyl]-1,2,4-oxadiazol-5-yl]-4-(3-nitrophenyl)pyridine-5-carboxylate.

31. The compound according to claim 3, which is methyl 1,4-dihydro-2,6-dimethyl-3-[3-(α-methylbenzylamino)methyl-1,2,4-oxadiazol-5-yl]-4-(3-nitrophenyl)pyridine-5-carboxylate.

32. A pharmaceutical composition for the treatment of hypertension, which comprises as an active ingredient an antihypertensively effective amount of at least one of the compounds of claim 1, and at least one pharmaceutically acceptable inert carrier or diluent.

33. A method of treating hypertension which comprises administering a antihypertensively effective amount of a compound of claim 1 to a patient.

* * * * *

UNITED STATES PATENT AND TRADEMARK OFFICE
CERTIFICATE OF CORRECTION

PATENT NO. : 4,705,786
DATED : November 10, 1987
INVENTOR(S) : YAMAMOTO et al

It is certified that error appears in the above—identified patent and that said Letters Patent are hereby corrected as shown below:

Column 40 (Claim 1), line 46, change "$R_{14}$" to --$R_8$--.

Column 40 (Claim 2), line 60, change "$R_{14}$ is $-T_3-R_9$" to --$R_8$ is $-T_3R_9$--.

Signed and Sealed this

Tenth Day of January, 1989

Attest:

DONALD J. QUIGG

Attesting Officer       Commissioner of Patents and Trademarks

UNITED STATES PATENT AND TRADEMARK OFFICE
CERTIFICATE OF CORRECTION

PATENT NO. : 4,705,786
DATED : November 10, 1987
INVENTOR(S) : Michihiro YAMAMOTO et al It is certified that error appears in the above-identified patent and that said Letters Patent is hereby corrected as shown below:

Title page:

<u>IN THE ABSTRACT</u>

Line 5 from the end of the Abstract, change

"or —$R_3R_9$" to

-- Wherein $R_8$ is —$T_3R_9$ --.

Signed and Sealed this

Fourth Day of April, 1989

*Attest:*

DONALD J. QUIGG

*Attesting Officer*   *Commissioner of Patents and Trademarks*